(12) United States Patent
Bryant et al.

(10) Patent No.: US 7,948,041 B2
(45) Date of Patent: May 24, 2011

(54) SENSOR HAVING A THIN-FILM INHIBITION LAYER

(75) Inventors: Craig Bryant, Alameda, CA (US); Ying-Lan Chang, Cupertino, CA (US); Jean-Christophe P. Gabriel, Quaix en Chartreuse (FR); Bradley N. Johnson, Berkeley, CA (US); Oleksandr Kuzmych, Emeryville, CA (US); William Mickelson, San Francisco, CA (US); John Loren Passmore, Berkeley, CA (US); Sergei Skarupo, Berkeley, CA (US); Christian Valcke, Orinda, CA (US)

(73) Assignee: Nanomix, Inc., Emeryville, CA (US)

( * ) Notice: Subject to any disclaimer, the term of this patent is extended or adjusted under 35 U.S.C. 154(b) by 479 days.

(21) Appl. No.: 11/924,328

(22) Filed: Oct. 25, 2007

(65) Prior Publication Data

US 2008/0221806 A1 Sep. 11, 2008

Related U.S. Application Data

(63) Continuation-in-part of application No. 11/636,360, filed on Dec. 8, 2006, and a continuation-in-part of application No. 11/588,845, filed on Oct. 26, 2006, now abandoned, application No. 11/924,328, which is a continuation-in-part of application No. 11/488,456, filed on Jul. 18, 2006, now abandoned, application No. 11/924,328, which is a continuation-in-part of application No. 11/437,275, filed on May 18, 2006, now abandoned.

(60) Provisional application No. 60/967,552, filed on Sep. 4, 2007, provisional application No. 60/922,642, filed on Apr. 10, 2007, provisional application No. 60/748,834, filed on Dec. 9, 2005, provisional application No. 60/730,905, filed on Oct. 27, 2005, provisional application No. 60/700,944, filed on Jul. 20, 2005, provisional application No. 60/683,460, filed on May 19, 2005.

(51) Int. Cl.
*H01L 27/14* (2006.01)

(52) U.S. Cl. ............ 257/414; 257/E31.119; 257/E33.06

(58) Field of Classification Search .................. 257/414, 257/252, 532, 288, 40, 30, E31.119, E33.06; 422/68.1, 129, 211, 198, 109; 702/22, 30; 977/962, 932, 953, 742
See application file for complete search history.

(56) References Cited

U.S. PATENT DOCUMENTS 3,079,232 A 2/1963 Andersen et al.
(Continued)

FOREIGN PATENT DOCUMENTS

EP 1 664 724 6/2006
(Continued)

OTHER PUBLICATIONS

Skudal et al., "Detection and identification of gaseous organics using a TiO2 sensor", 2002, Journal of Photochemistry and Photobiology. A: Chemistry, vol. 148, pp. 103-108.*

(Continued)

*Primary Examiner* — Thomas L Dickey
*Assistant Examiner* — Nikolay Yushin
(74) *Attorney, Agent, or Firm* — Weaver Austin Villeneuve & Sampson LLP

(57) ABSTRACT

Sensors and detection systems suitable for measuring analytes, such as biomolecule, organic and inorganic species, including environmentally and medically relevant volatiles and gases, such as NO, NO2, CO2, NH3, H2, CO and the like, are provided. Certain embodiments of nanostructured sensor systems are configured for measurement of medically important gases in breath. Applications include the measurement of endogenous nitric oxide (NO) in breath, such as for the monitoring or diagnosis of asthma and other pulmonary conditions.

21 Claims, 11 Drawing Sheets

U.S. PATENT DOCUMENTS

| | | |
|---|---|---|
| 3,860,430 A | 1/1975 | Walker et al. |
| 4,022,059 A | 5/1977 | Schontzler et al. |
| 4,333,735 A | 6/1982 | Hardy et al. |
| 4,502,938 A | 3/1985 | Covington et al. |
| 4,777,019 A | 10/1988 | Dandekar |
| 4,795,968 A | 1/1989 | Madou et al. |
| 4,836,898 A | 6/1989 | Noyes |
| 4,851,195 A | 7/1989 | Matthews et al. |
| 4,909,919 A | 3/1990 | Morris et al. |
| 4,935,345 A | 6/1990 | Guilbeau et al. |
| 5,213,770 A | 5/1993 | Noyes |
| 5,246,859 A | 9/1993 | Nelson et al. |
| 5,258,415 A | 11/1993 | Hahn et al. |
| 5,334,351 A | 8/1994 | Heinze |
| 5,382,417 A | 1/1995 | Haase |
| 5,425,869 A | 6/1995 | Noding et al. |
| 5,448,905 A | 9/1995 | Stetter et al. |
| 5,569,455 A | 10/1996 | Fukui et al. |
| 5,618,496 A | 4/1997 | Hasumi et al. |
| 5,674,752 A | 10/1997 | Buckley et al. |
| 5,827,997 A | 10/1998 | Chung et al. |
| 5,958,340 A | 9/1999 | Meyer et al. |
| 5,993,694 A | 11/1999 | Ito et al. |
| 6,004,494 A | 12/1999 | Debe |
| 6,010,459 A | 1/2000 | Silkoff et al. |
| 6,031,454 A | 2/2000 | Lovejoy et al. |
| 6,044,843 A | 4/2000 | O'Neil et al. |
| 6,060,327 A | 5/2000 | Keen |
| 6,066,448 A | 5/2000 | Wohlstadter et al. |
| 6,090,545 A | 7/2000 | Wohlstadter et al. |
| 6,111,280 A | 8/2000 | Gardner et al. |
| 6,136,962 A | 10/2000 | Shi et al. |
| 6,217,828 B1 | 4/2001 | Bretscher et al. |
| 6,286,226 B1 | 9/2001 | Jin |
| 6,287,874 B1 | 9/2001 | Hefti |
| 6,297,059 B1 | 10/2001 | Song et al. |
| 6,320,295 B1 | 11/2001 | McGill et al. |
| 6,326,215 B1 | 12/2001 | Keen |
| 6,329,209 B1 | 12/2001 | Wagner et al. |
| 6,346,189 B1 | 2/2002 | Dai et al. |
| 6,426,231 B1 | 7/2002 | Bayley |
| 6,444,318 B1 | 9/2002 | Guire et al. |
| 6,445,006 B1 | 9/2002 | Brandes et al. |
| 6,465,132 B1 | 10/2002 | Jin |
| 6,489,394 B1 | 12/2002 | Andros |
| 6,528,020 B1 | 3/2003 | Dai et al. |
| 6,577,242 B2 | 6/2003 | Jen et al. |
| 6,628,053 B1 | 9/2003 | Den et al. |
| 6,656,712 B1 | 12/2003 | Balavoine et al. |
| 6,656,835 B2 | 12/2003 | Marsh et al. |
| 6,676,904 B1 | 1/2004 | Lee et al. |
| 6,797,325 B2 | 9/2004 | Wang et al. |
| 6,894,359 B2 | 5/2005 | Bradley et al. |
| 6,905,655 B2 | 6/2005 | Gabriel et al. |
| 7,013,708 B1 | 3/2006 | Cho et al. |
| 7,109,859 B2 | 9/2006 | Peeters |
| 7,271,720 B2 | 9/2007 | Tabe |
| 7,312,095 B1 | 12/2007 | Gabriel et al. |
| 7,347,974 B1 | 3/2008 | Snow et al. |
| 7,449,757 B2 | 11/2008 | Bradley et al. |
| 7,522,040 B2 | 4/2009 | Passmore et al. |
| 7,547,931 B2 | 6/2009 | Star et al. |
| 2002/0014667 A1 | 2/2002 | Shin et al. |
| 2002/0092779 A1 | 7/2002 | Essalik et al. |
| 2002/0117659 A1 | 8/2002 | Lieber et al. |
| 2002/0118027 A1 | 8/2002 | Routkevitch et al. |
| 2002/0123048 A1 | 9/2002 | Gau |
| 2002/0130333 A1 | 9/2002 | Watanabe et al. |
| 2002/0172639 A1 | 11/2002 | Horiuchi et al. |
| 2002/0172963 A1 | 11/2002 | Kelley et al. |
| 2002/0179434 A1 | 12/2002 | Dai et al. |
| 2003/0031620 A1 | 2/2003 | Harutyunyan et al. |
| 2003/0041438 A1 | 3/2003 | Wei et al. |
| 2003/0068432 A1 | 4/2003 | Dai et al. |
| 2003/0073071 A1 | 4/2003 | Fritz et al. |
| 2003/0073919 A1 | 4/2003 | Hampton et al. |
| 2003/0113713 A1 | 6/2003 | Glezer et al. |
| 2003/0134267 A1 | 7/2003 | Kang et al. |
| 2003/0134433 A1 | 7/2003 | Gabriel et al. |
| 2003/0139003 A1 | 7/2003 | Gole et al. |
| 2003/0171257 A1 | 9/2003 | Stirbl et al. |
| 2003/0175161 A1 | 9/2003 | Gabriel et al. |
| 2003/0180640 A1 | 9/2003 | Darty |
| 2003/0199172 A1 | 10/2003 | Rueckes et al. |
| 2004/0011291 A1 | 1/2004 | Delaunay et al. |
| 2004/0018587 A1 | 1/2004 | Makowski et al. |
| 2004/0023428 A1 | 2/2004 | Gole et al. |
| 2004/0029297 A1 | 2/2004 | Bonnell et al. |
| 2004/0043527 A1* | 3/2004 | Bradley et al. .................. 438/48 |
| 2004/0065970 A1 | 4/2004 | Blanchet-Fincher |
| 2004/0067530 A1 | 4/2004 | Gruner |
| 2004/0091285 A1 | 5/2004 | Lewis |
| 2004/0104129 A1 | 6/2004 | Gu et al. |
| 2004/0119141 A1* | 6/2004 | Schreiter et al. .............. 257/532 |
| 2004/0120183 A1 | 6/2004 | Appenzeller et al. |
| 2004/0132070 A1 | 7/2004 | Star et al. |
| 2004/0136866 A1 | 7/2004 | Pontis et al. |
| 2004/0158410 A1 | 8/2004 | Ono et al. |
| 2004/0188780 A1 | 9/2004 | Kurtz |
| 2004/0192072 A1 | 9/2004 | Snow et al. |
| 2004/0200734 A1 | 10/2004 | Co et al. |
| 2004/0202603 A1 | 10/2004 | Fischer et al. |
| 2004/0204915 A1 | 10/2004 | Steinthal et al. |
| 2004/0211580 A1 | 10/2004 | Wang et al. |
| 2005/0065741 A1 | 3/2005 | Segal et al. |
| 2005/0072213 A1 | 4/2005 | Besnard et al. |
| 2005/0103097 A1 | 5/2005 | Faltum et al. |
| 2005/0112052 A1 | 5/2005 | Gu et al. |
| 2005/0129573 A1 | 6/2005 | Gabriel et al. |
| 2005/0135982 A1 | 6/2005 | Pavlovsky |
| 2005/0157445 A1 | 7/2005 | Bradley et al. |
| 2005/0169798 A1 | 8/2005 | Bradley et al. |
| 2005/0211572 A1 | 9/2005 | Buck et al. |
| 2005/0245836 A1 | 11/2005 | Star et al. |
| 2005/0279987 A1 | 12/2005 | Star et al. |
| 2006/0009707 A1 | 1/2006 | Daniels et al. |
| 2006/0009797 A1 | 1/2006 | Armstrong |
| 2006/0021881 A1 | 2/2006 | Soundarrajan et al. |
| 2006/0054936 A1 | 3/2006 | Lieber et al. |
| 2006/0055392 A1 | 3/2006 | Passmore et al. |
| 2006/0058266 A1 | 3/2006 | Manoharan et al. |
| 2006/0102494 A1 | 5/2006 | Chueh et al. |
| 2006/0213187 A1 | 9/2006 | Kupe et al. |
| 2006/0232278 A1 | 10/2006 | Diamond et al. |
| 2006/0249402 A1 | 11/2006 | Snow et al. |
| 2006/0263255 A1 | 11/2006 | Han et al. |
| 2007/0048180 A1 | 3/2007 | Gabriel et al. |
| 2007/0114138 A1 | 5/2007 | Krasteva et al. |
| 2007/0114573 A1 | 5/2007 | Han et al. |
| 2007/0132043 A1 | 6/2007 | Bradley et al. |
| 2007/0158642 A1* | 7/2007 | Gruner ........................... 257/40 |
| 2007/0208243 A1 | 9/2007 | Gabriel et al. |
| 2007/0259359 A1 | 11/2007 | Briman et al. |
| 2008/0021339 A1 | 1/2008 | Gabriel et al. |
| 2008/0093226 A1 | 4/2008 | Briman et al. |
| 2009/0056419 A1 | 3/2009 | Chang et al. |
| 2009/0101996 A1 | 4/2009 | Bradley et al. |
| 2009/0165533 A1 | 7/2009 | Han |
| 2010/0085067 A1 | 4/2010 | Gabriel et al. |
| 2010/0137731 A1 | 6/2010 | Star et al. |
| 2010/0231242 A1 | 9/2010 | Gabriel et al. |

FOREIGN PATENT DOCUMENTS

| | | |
|---|---|---|
| EP | 1 680 353 | 7/2006 |
| EP | 1 941 270 | 7/2008 |
| JP | 2002-503204 | 1/2002 |
| JP | 2003-517604 | 5/2003 |
| JP | 2005-507121 | 3/2005 |
| WO | WO 97/32571 | 9/1997 |
| WO | WO 01/32951 | 5/2001 |
| WO | WO 01/44796 | 6/2001 |
| WO | WO 02/15240 | 2/2002 |
| WO | WO 02/48701 | 6/2002 |
| WO | WO 02/054052 | 7/2002 |
| WO | WO 02/079514 | 10/2002 |
| WO | WO 02/095099 | 11/2002 |
| WO | WO 2003/016901 | 2/2003 |

| | | |
|---|---|---|
| WO | WO 2003/046536 | 6/2003 |
| WO | WO 2004/044586 | 5/2004 |
| WO | WO 2005/026694 | 3/2005 |
| WO | WO 2005/062031 | 7/2005 |
| WO | WO 2005/094221 | 10/2005 |
| WO | WO 2007/136523 | 11/2007 |
| WO | WO 2008/039165 | 4/2008 |
| WO | WO 2008/052104 | 5/2008 |
| WO | WO 2009/032534 A1 | 3/2009 |

OTHER PUBLICATIONS

Perkins et al., "Electrical and material properties of ZrO2 gate dielectrics grown by atomic layer chemical vapor deposition", 2001, Applied Physics letters, vol. 78, No. 18, pp. 2357-2359.*

Gabriel, "Large scale production of carbon nanotube transistors: a general platform for chemical sensors", 2003, Mat. Res. Soc. Symp. Proc., vol. 776, pages.*

U.S. Appl. No. 11/318,354, filed Dec. 23, 2005, Gabriel et al.

U.S. Appl. No. 11/541,794, filed Oct. 2, 2006, Gabriel et al.

U.S. Appl. No. 12/193,353, filed Aug. 18, 2008, Chang et al.

US Office Action dated Dec. 12, 2007 issued in U.S. Appl. No. 10/655,529.

US Office Action Final dated Jul. 3, 2008 issued in U.S. Appl. No. 10/655,529.

US Advisory Action dated Sep. 22, 2008 issued in U.S. Appl. No. 10/655,529.

US Notice of Abandonment dated Mar. 18, 2009 issued in U.S. Appl. No. 10/655,529.

US Notice of Abandonment dated Jan. 29, 2010 issued in U.S. Appl. No. 11/354,561.

US Notice of Abandonment dated May 6, 2010 issued in U.S. Appl. No. 12/245,638.

US Office Action dated Mar. 17, 2006 issued in U.S. Appl. No. 10/656,898.

US Office Action Final dated Oct. 20, 2006 issued in U.S. Appl. No. 10/656,898.

US Office Action dated May 7, 2007 issued in U.S. Appl. No. 10/656,898.

US Office Action Final dated Jan. 17, 2008 issued in U.S. Appl. No. 10/656,898.

US Advisory Action dated Apr. 8, 2008 issued in U.S. Appl. No. 10/656,898.

US Office Action dated Jul. 24, 2008 issued in U.S. Appl. No. 10/656,898.

US Notice of Abandonment dated Jan. 30, 2009 issued in U.S. Appl. No. 10/656,898.

US Office Action dated Jul. 14, 2008 issued in U.S. Appl. No. 11/019,792.

US Notice of Allowance dated Feb. 21, 2009 issued in U.S. Appl. No. 11/019,792.

US Office Action dated Jul. 26, 2010 issued in U.S. Appl. No. 12/485,793.

US Office Action dated May 12, 2008 issued in U.S. Appl. No. 11/437,275.

US Office Action Final dated Feb. 3, 2009 issued in U.S. Appl. No. 11/437,275.

US Office Action (Notice of Abandonment) dated Sep. 11, 2009 issued in U.S. Appl. No. 11/437,275.

US Office Action dated Mar. 17, 2009 issued in U.S. Appl. No. 11/588,845.

US Office Action (Notice of Abandonment) dated Oct. 1, 2009 issued in U.S. Appl. No. 11/588,845.

US Office Action dated Oct. 7, 2010 issued in U.S. Appl. No. 12/560,316.

US Office Action Restriction Requirement and Examiner Interview Summary dated Dec. 3, 2009 issued in U.S. Appl. No. 11/636,360.

US Office Action dated Mar. 24, 2010 issued in U.S. Appl. No. 11/636,360.

US Office Action Final dated Nov. 4, 2010 issued in U.S. Appl. No. 11/636,360.

US Office Action dated Jun. 1, 2005 issued in U.S. Appl. No. 10/940,324.

US Office Action dated Mar. 3, 2006 issued in U.S. Appl. No. 10/940,324.

US Office Action dated Sep. 7, 2006 issued in U.S. Appl. No. 10/940,324.

US Office Action Final dated Feb. 21, 2007 issued in U.S. Appl. No. 10/940,324.

US Office Action dated Aug. 27, 2007 issued in U.S. Appl. No. 10/940,324.

US Examiner Summary dated Feb. 1, 2008 issued in U.S. Appl. No. 10/940,324.

US Office Action Final dated May 27, 2008 issued in U.S. Appl. No. 10/940,324.

US Office Action dated Aug. 12, 2008 issued in U.S. Appl. No. 10/940,324.

US Office Action dated Apr. 16, 2009 issued in U.S. Appl. No. 10/940,324.

US Notice of Abandonment dated Nov. 25, 2009 issued in U.S. Appl. No. 10/940,324.

US Office Action dated Apr. 1, 2008 issued in U.S. Appl. No. 11/111,121.

US Office Examiner Interview Summary dated Sep. 23, 2008 issued in U.S. Appl. No. 11/111,121.

US Notice of Allowance dated Oct. 8, 2008 issued in U.S. Appl. No. 11/111,121.

US Office Action dated Dec. 2, 2005 issued in U.S. Appl. No. 10/945,803.

US Office Action Final dated Apr. 6, 2007 issued in U.S. Appl. No. 10/945,803.

US Office Action Final dated Sep. 12, 2007 issued in U.S. Appl. No. 10/945,803.

US Office Action dated Jun. 12, 2008 issued in U.S. Appl. No. 10/945,803.

US Notice of Allowance dated Jul. 7, 2008 issued in U.S. Appl. No. 10/945,803.

US Office Action Final dated Nov. 2, 2009 issued in U.S. Appl. No. 12/268,327.

US Office Action dated May 15, 2006 issued in U.S. Appl. No. 10/345,783.

US Final Office Action dated Dec. 22, 2006 issued in U.S. Appl. No. 10/345,783.

US Advisory Action dated Apr. 3, 2007 issued in U.S. Appl. No. 10/345,783.

US Office Action dated Jul. 24, 2007 issued in U.S. Appl. No. 10/345,783.

US Final Office Action dated May 22, 2008 issued in U.S. Appl. No. 10/345,783.

US Advisory Action dated Aug. 27, 2008 issued in U.S. Appl. No. 10/345,783.

US Final Office Action dated Nov. 12, 2008 issued in U.S. Appl. No. 10/345,783.

US Final Office Action dated Jun. 10, 2009 issued in U.S. Appl. No. 10/345,783.

US Notice of Abandonment dated Jan. 7, 2010 issued in U.S. Appl. No. 10/345,783.

US Office Action dated Jul. 23, 2010 issued in U.S. Appl. No. 12/634,525.

US Office Action dated Jun. 1, 2006 issued in U.S. Appl. No. 10/704,066.

US Office Action Final dated Jan. 24, 2007 issued in U.S. Appl. No. 10/704,066.

US Office Action dated Aug. 24, 2007 issued in U.S. Appl. No. 10/704,066.

US Notice of Abandonment and Examiner Interview Summary dated Mar. 6, 2008 issued in U.S. Appl. No. 10/704,066.

US Office Action dated Mar. 4, 2008 issued in U.S. Appl. No. 11/318,354.

US Office Action dated Feb. 24, 2009 issued in U.S. Appl. No. 11/318,354.

US Notice of Abandonment dated Sep. 15, 2009 issued in U.S. Appl. No. 11/318,354.

US Office Action dated Feb. 25, 2008 issued in U.S. Appl. No. 11/274,747.

US Examiner Interview Summary dated May 28, 2008 issued in U.S. Appl. No. 11/274,747.
US Office Action Final dated Feb. 11, 2009 issued in U.S. Appl. No. 11/274,747.
US Notice of Abandonment dated May 11, 2009 issued in U.S. Appl. No. 11/274,747.
US Office Action dated Oct. 3, 2008 issued in U.S. Appl. No. 11/400,038.
US Office Action Final dated Jul. 7, 2009 issued in U.S. Appl. No. 11/400,038.
US Notice of Allowance dated Jan. 4, 2005 issued in U.S. Appl. No. 10/280,265.
US Office Action dated Jan. 18, 2008 issued in U.S. Appl. No. 11/090,550.
US Office Action Final dated Oct. 30, 2008 issued in U.S. Appl. No. 11/090,550.
US Office Action dated Apr. 15, 2009 issued in U.S. Appl. No. 11/090,550.
US Office Action Final dated Jan. 19, 2010 issued in U.S. Appl. No. 11/090,550.
US Office Action dated Jul. 13, 2010 issued in U.S. Appl. No. 12/193,353.
PCT International Search Report and Written Opinion dated Jun. 11, 2008 issued in WO 2008/039165.
International Preliminary Report on Patentability and Written Opinion dated Jul. 1, 2008 issued in WO 2008/039165.
PCT International Search Report dated Aug. 7, 2008 issued in PCT/US2007/10836.
PCT International Preliminary Report on Patentability and Written Opinion dated Nov. 18, 2008 issued in PCT/US07/10836.
PCT International Search Report dated Sep. 22, 2005 issued in WO 2005/026694.
PCT International Preliminary Report on Patentability and Written Opinion dated Jul. 31, 2006 issued in WO 2005/026694.
European Search Report dated Mar. 30, 2007 issued in EP 04 788 761.7.
European Examination Report dated Feb. 10, 2010 issued in EP 04 788 761.7.
Japanese Office Action dated Jul. 13, 2010 issued in JP 2006-526418.
PCT International Search Report dated Nov. 6, 2007 issued in WO 2005/094221.
PCT International Preliminary Examination Report and Written Opinion dated Nov. 23, 2007 issued in WO 2005/094221
PCT International Search Report dated Mar. 30, 2004 issued in WO 2004/044586.
PCT International Preliminary Examination Report dated Nov. 16, 2006 issued in WO 2004/044586.
European Examination Report dated May 19, 2006 issued in EP03768779.5.
European Examination Report dated Dec. 22, 2009 issued in EP03768779.5.
European Examination Report dated Jul. 13, 2010 issued in EP03768779.5.
Japanese Office Action issued Oct. 8, 2009 issued in JP2005-507121 (as translated by foreign associate in letter dated Nov. 2, 2009), 3pgs.
PCT International Search Report dated Jun. 11, 2008 issued in WO 2008/052104.
PCT International Preliminary Report on Patentability and Written Opinion dated Jun. 11, 2008 issued in WO2008/052104.
PCT International Search Report dated Nov. 19, 2008 issued in PCT/US08/73746 (WO2009/032534).
PCT International Preliminary Report on Patentability and Written Opinion dated Mar. 9, 2010 issued in PCT/US08/73746 (WO 2009/032534).
Appenzeller et al., (2001) "Optimized contact configuration for the study of transport phenomena in ropes of single-wall carbon nanotubes", *Appl Phys. Lett.* 78(1):3313-3315.
Avouris et al., "Molecular electronics with carbon nanotubes," *Accounts of Chemical Research*, [10.1021/ar010152e] [Web Release Date: Jul. 31, 2002] 35:1026-1034.
Balavoine et al., (1999) *Angew. Chem. Int.. Ed*, 38, No. 13/14:1912-1915.
Bradley et al., (2000) *Phys. Rev. Lett.* 85(20):4361-4364.

Chen et al., (2001) *J. Am. Chem. Soc.*, 123:3838-3839.
Chen et al., (2004) "CO selective oxidation in a microchannel reactor for PEM fuel cell", *Chemical Engineering Journal*, 101:101-106.
Collins et al., (2000) "Extreme oxygen sensitivity of electronic properties of carbon nanotubes," *Science*, 287:1801-1804.
Collins et al., (2001) "Current Saturation and Electrical breakdown in Multiwalled Carbon Nanotubes," *Phys. Rev. Lett.*, 86(14):3128-3131.
Collins et al., (Apr. 27, 2001) "Engineering Carbon Nanotubes and Nanotube Circuits Using Electrical Breakdown," *Science*, 292:706-709.
Cui, Yi et al., (2001) "Nanowire Nanosensors for Highly Sensitive and Selective Detection of Biological and Chemical Species," *Science*, 293:1289-1292.
Cui et al., (2002) "Room Temperature Single Electron Transistor by Local Chemical Modification of Carbon Nanotubes" *Nano Letters* 2(2):117-120.
Dai, H., (2002) "Carbon nanotubes: opportunities and challenges," *Surface Science*, 500:218-241.
Derycke et al., (Sep. 2001) "Carbon Nanotube Inter-and Intramolecular Logic Gates," *Nano Letters*, 1(9):453-456.
Derycke et al., (2002) "Controlling doping and carrier injection in carbon nanotube transistors, "*Appl. Phys. Lett.* 80(15):2773-2775.
Hansson et al., (2000) *Phys. Rev. B*, 62(11):7639-7644.
Heinze et al., (2002) "Carbon nanotubes as Schottky barrier Transistors," *Phys. Rev. Lett.* 89(10):106801-(1-4).
Jhi et al., (2000) *Phys Rev. Lett.*, 85(8):1710-1713.
Kemell et al., (2006) "Ir/Oxide/Cellulose Composites for Catalytic Purposes Prepared by Atomic Layer Deposition", *Chem. Vap. Deposition*, 12:419-422; [Published Online: Jul. 6, 2006].
Kim et al., (2001) *Phys. Rev. B*, 64(15):153404-(1-4).
Kim et al., (2005) "Atomic Layer Deposition of Pd on TaN for Cu Electroless Plating", *Journal of The Electrochemical Society*, 152(6):C376-C381.
Knobler et al., (1999) *Current Opinion in Colloid & Interface Science*, 4:46-51.
Kong et al., (2000) "Nanotube Molecular Wires as Chemical Sensors," *Science*, 287:622-625.
Kong et al., (2001) "Functionalized Carbon Nanotubes for Molecular Hydrogen Sensors," *Adv. Mater*, 13(18):1384-1386.
Kong et al., (Jan. 7, 2002) "Chemical Profiling of Single Nanotubes: Intromolecular p-n-p Junctions and On-Tube Single-Electron Transistors", *Appl Phys Let.*, 80(1):73-75.
Leonard et al., (1999) *Phys. Rev. Lett.*, 83(24):5174-5177.
Lin, Yi et al., (2002) "Functionalization Multiple-Walled Carbon Nanotubes with Aminopolymers," *Jnl of Phy Chem, B, Materials, Surfaces, Interfaces and Biophysical*, Washington DC U.S. 106(6)1294-1298; XP002971880, Washington, DC, U.S.
Liu et al., (2001) *Phys. Rev. B*, 64(3):033412-(1-4).
Martel et al., (2001) *Phys. Rev. Lett.*, 87(25):256805-(1-4).
Ng, H.T. et al., (Dec. 2001) "Flexible Carbon Nanotube Membrane Sensory System: A Generic Platform", *Journal of Nanoscience and Nanotechnology*, 1(4):375-379.
Okada et al., (2001) *Journal of the Physical Society of Japan*, 70(8) p. 2345-2352.
Ong et al., (Nov. 2, 2001) "A Carbon Nanotube-based Sensor for $CO_2$ Monitoring", *SENSORS, MDPT, BASEL, SU*, 1(6):193-205.
Qi et al., (2003) "Toward Large Arrays of Multiplex Functionalized Carbon Nanotube Sensors for Highly Sensitive and Selective Molecular Detection", *Nano Letters*, 3(3):347-351.
Radosavljevic et al., (2001) "High-field electrical transport and breakdown in bundles of single-wall carbon nanotubes," *Phy. Rev. B*. 64, pp. 241307-1 to 241307-4.
Schwartz, (1997) *Surface Science Reports*, 27:241-334.
Shim et al., (2001) "Polymer Functionalization for Air-Stable n-Type Carbon Nanotube Field-Effect Transistors," *J Am. Chem Soc.*, 123(46):11512-11513.
Shim et al., (2002) "Functionalization of Carbon Nanotubes for Biocompatibility and Biomolecular Recognition," *Nano Letter*, 2(4):285-288, Published on Web Jan. 25, 2002.
Simon, (2001) "Micromachined metal Oxide gas sensors: opportunities to improve sensor performance," *Sensors and Actuators*, 73:1-26.

Soh, H.T. et al., (Aug. 2, 1999) "Integrated Nanotube Circuits: Controlled Growth and Ohmic Contacting of Single-Walled Carbon Nanotubes," *Appl. Phys. Lett.*, 75(5):627-629.

Stetter et al., (Feb. 23, 2003) "Nano-Electronic Sensors; Practical Device Designs for Sensors", *Nanotechnology Conference and Trade Show, Nanotech, Joint Meeting, International Conference on Modeling and Simulation of Microsystems, MSM, International Conference on Computational Nanoscience and Technology*, 3(23):313-316.

Suri et al., (2002) "Gas and Humidity Sensors Based on Iron Oxide-Polypyrrole Nanocomposites," *Sensors and Actuators*, B81:277-282.

Szabo et al., (2003) "Strategies for total $No_x$ measurement with minimal CO interference utilizing a microporous zeolitic catalytic filter", *Sensors and Actuators B*, 88:168-177.

Zhou, C. et al., (Nov. 24, 2000) "Modulated Chemical Doping of Individual Carbon Nanotubes" *SCIENCE*, 290:1552-1555.

* cited by examiner

FIG. 2 (views a -d)

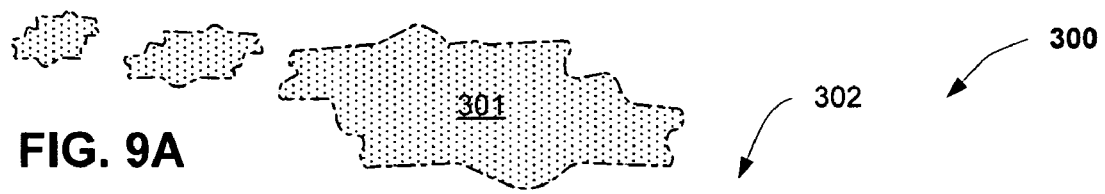
FIG. 9A
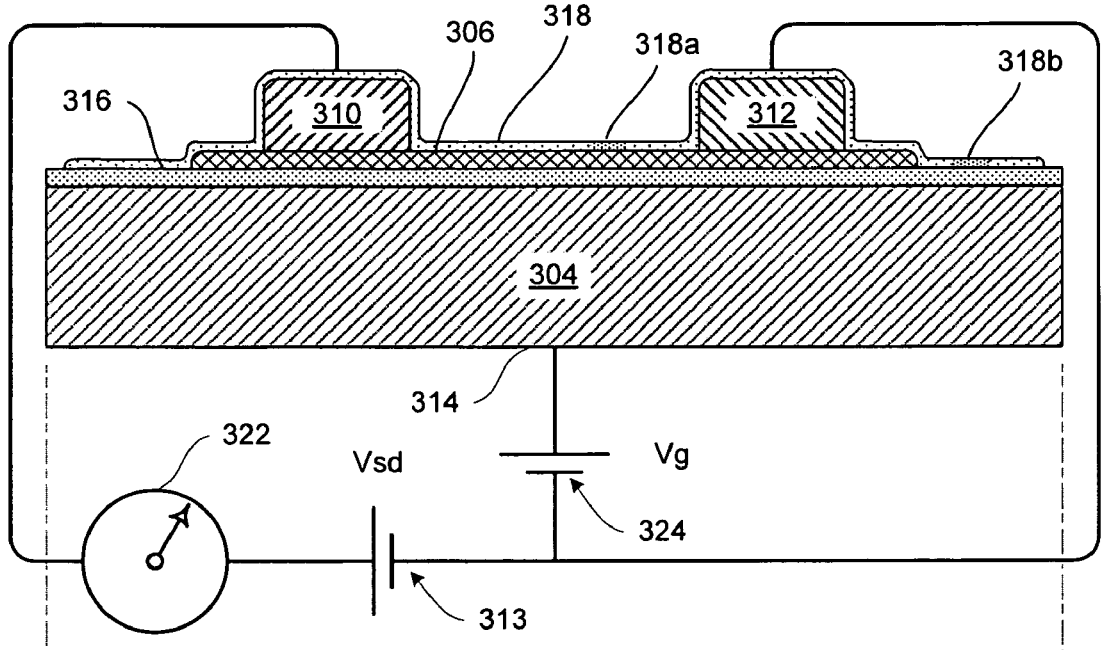
FIG. 9B
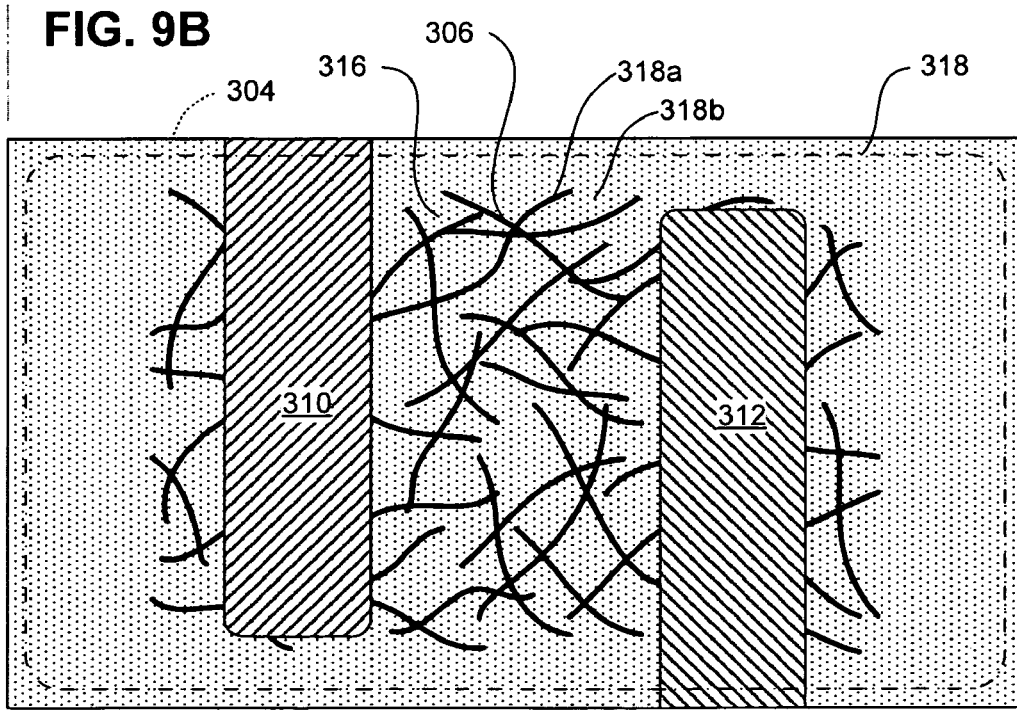

breath NO depencency on exhalation rate
(from US Patent No. 6,733,463)

NO breath profile

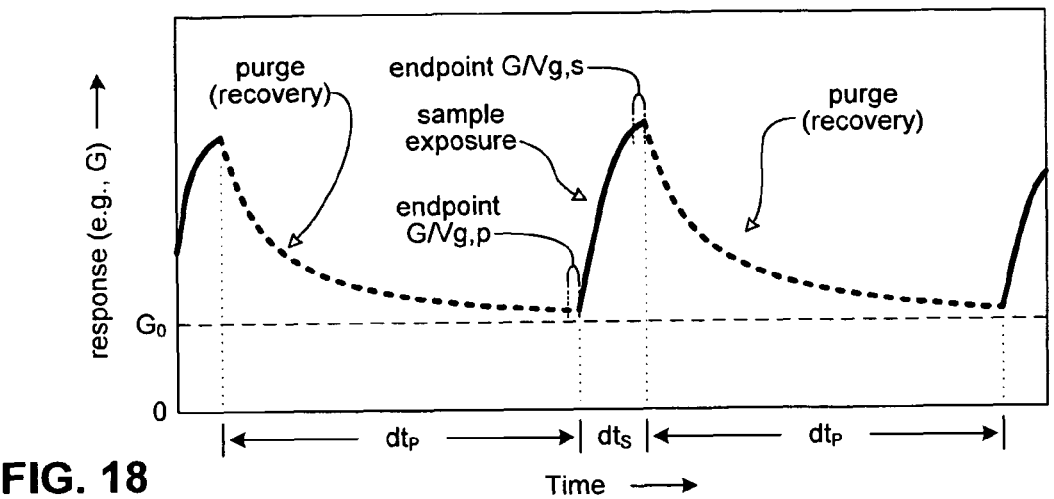
FIG. 18
FIG. 19
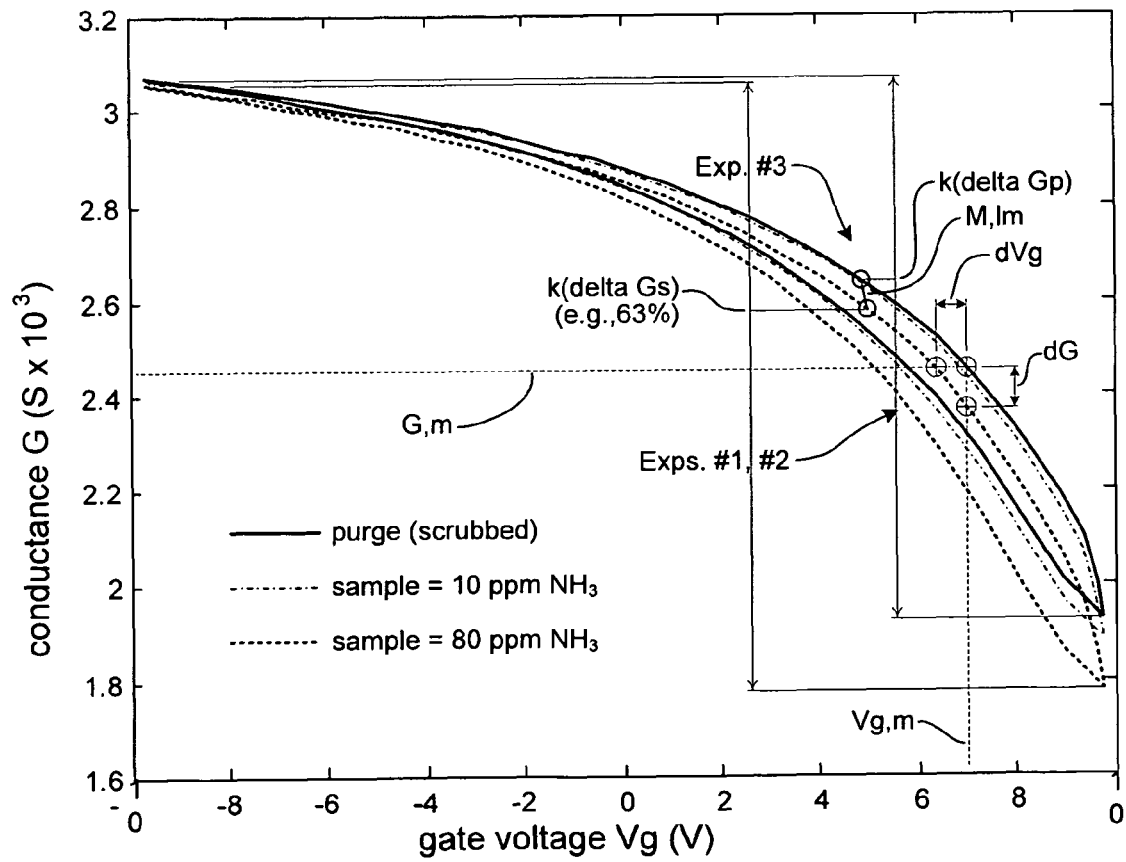

US 7,948,041 B2

SENSOR HAVING A THIN-FILM INHIBITION LAYER

CROSS-REFERENCE TO RELATED APPLICATIONS

This application claims the benefit pursuant to 35 USC. 119(e) of the following US Provisional Applications, each of which applications are incorporated by reference:

U.S. Application No. 60/967,552 filed Sep. 4, 2007, entitled "Sensor Having A Thin-Film Inhibition Layer, Nitric Oxide Converter And Monitor"; and U.S. Application No. 60/922,642 filed Apr. 10, 2007, entitled "Ammonia Nanosensors, and Environmental Control System";

This application claims priority pursuant to 35 USC. §120 of the following U.S. Applications, each of which applications are incorporated by reference:

U.S. Ser. No. 11/636,360 filed Dec. 8, 2006 (published 2008-0093226), entitled "Ammonia Nanosensors, and Environmental Control System"; which claims priority to US provisional application. No. 60/748,834 filed Dec. 9, 2005;

U.S. Ser. No. 11/588,845 filed Oct. 26, 2006 (published 2008-0021339), entitled "Anesthesia Monitor, Capacitance Nanosensors and Dynamic Sensor Sampling Method"; which claims priority to US provisional application No. 60/730,905 filed Oct. 27, 2005;

U.S. Ser. No. 11/488,456 filed Jul. 18, 2006 (published 2007-0048,181) entitled "Improved Carbon Dioxide Nanosensor, And Respiratory CO2 Monitors"; which claims priority to U.S. provisional application No. 60/700,944 filed Jul. 20, 2005; and U.S. Ser. No. 11/437,275 filed May 18, 2006 (published 2007-0048,180) entitled "Nanoelectronic Breath Analyzer and Asthma Monitor"; which claims priority to U.S. provisional application No. 60/683,460, filed May 19, 2005.

Each of the following patent applications is incorporated by this reference in its entirety for all purposes and relates to aspects of the invention in some manner:

U.S. Ser. No. 11/541,794 filed Oct. 2, 2006 (published 2010-0323925), entitled "Sensor Array Based On Metal Decorated Carbon Nanotubes";

U.S. Ser. No. 11/259,414 filed Oct. 25, 2005 (published 2006-0228,723), entitled "Systems and method for electronic detection of biomolecules"; which claims priority to No. 60/622,468 filed Oct. 25, 2004;

U.S. Ser. No. 11/019,792 filed Dec. 18, 2004 (published 2005-0245,836), entitled "Nanoelectronic Capnometer Adapter"";

U.S. Ser. No. 10/940,324 filed Sep. 13, 2004 (published 2005-0129,573), entitled "Carbon Dioxide Nanoelectronic Sensor";

U.S. Ser. No. 10/656,898 filed Sep. 5, 2003 (published 2005-0279,987), entitled "Polymer Recognition Layers For Nanostructure Sensor Devices";

U.S. Ser. No. 11/090,550 filed Mar. 25, 2005 (Pat. No. 6,894,359), entitled "Sensitivity Control For Nanotube Sensors";

U.S. Ser. No. 10/177,929 filed Jun. 21, 2002 (equivalent publication U.S. 2007-0140,946), entitled "Dispersed Growth Of Nanotubes On A Substrate" ; and U.S. Ser. No. 10/388,701 filed Mar. 14, 2003 (Pat. No. 6,905,655), entitled "Modification Of Selectivity For Sensing For Nanostructure Device Arrays".

BACKGROUND

1. Field of the Invention

The present invention relates to nanostructured sensor systems for measurement analytes, for example by measurement of variations of electrical properties of nanostructure elements in response to an analyte, such as biomolecule, organic and inorganic species, including environmentally and medically relevant volatiles and gases, such as NO, $NO_2$, $CO_2$, $NH_3$, $H_2$, CO and the like. Certain embodiments of nanostructured sensor systems are configured for measurement of medically important gases in breath. Examples are described relating to the measurement of endogenous nitric oxide in breath, such as for the monitoring or diagnosis of asthma and other pulmonary conditions.

2. Description of Related Art

The measurement of carbon dioxide levels in respiration is a standard procedure during intensive care and anesthesia and is a primary tool in the diagnosis and management of respiratory function. In addition to the measurement of $CO_2$, medical breath analysis and monitoring may employ measurements of many other chemical species to improve diagnosis and patient care. In general, exhaled breath has a composition which is distinct from inspired air. Compounds are either removed from inspired air (e.g., oxygen as $O_2$ is absorbed and metabolized) or added to exhaled breath (e.g., $CO_2$, $H_2O$). In addition, treatment compounds (e.g., anesthetic agents) may be added to inspired air for inhaled administration, and may be detected in exhaled breath.

Although the substantial portions of exhaled breath include $N_2$, $O_2$, $CO_2$, water vapor and other atmospheric constituents (e.g., argon and the like), many volatile organic and inorganic chemical species which are produced by metabolic processes within the body are released in exhaled breath (often in only trace amounts). Such metabolic species often have medical significance. For example, nitric oxide (NO), nitrogen dioxide ($NO_2$), other nitrogen-containing compounds, sulfur-containing compounds, hydrogen peroxide, carbon monoxide, hydrogen, ammonia, ketones, aldehydes, esters, alkanes, and other volatile organic compounds may be present in exhaled breath. Medical conditions related to such metabolic exhaled breath constituents include tissue inflammation (e.g. asthma), immune responses (e.g. to cancer cells or bacteria), metabolic problems (e.g. diabetes), digestive processes, liver problems, kidney problems, heart problems, gum disease, halitosis, blood component levels, and other physiological conditions.

NO detection in breath is a proven marker for airway inflammation (as well as for other tissue inflammation, immune responses, and other conditions). Therefore, the ability to measure NO as an exhaled breath parameter, for example as fractional exhaled nitric oxide (FeNO), is a valuable tool for diagnosis, monitoring, and managed treatment of asthma and other disorders. See, for example, U.S. Pat. No. 6,010,459 entitled "Method and apparatus for the measurement of components of exhaled breath in humans", which is incorporated by reference. However, medical systems for the measurement of NO suffer from generally the same limitations as capnograph devices, e.g., high cost, weight and complexity.

$CO_2$ detection in breath has been used as an indicator of perfusion and heart function as well as ventilator effectiveness. In addition, $CO_2$ is useful, by itself or in combination with other measurements, in diagnosing and monitoring airway status and pulmonary function. For example, see U.S. Pat. No. 6,648,833 entitled "Respiratory analysis with capnography", which is incorporated by reference.

It has also been proposed to monitor medical conditions, such as asthma, using detection of more than one metabolic species, for example considering both NO and CO2 in exhaled breath. For example, see US Published Application No. 2003-0134,427 entitled "Method and apparatus for determining gas concentration"; and C. Roller et al., "Simultaneous NO and CO2 measurement in human breath with a single IV-VI mid-infrared laser", Optics Letters (2002) Vol. 27, No. 2, pgs. 107-109; each of which is incorporated by reference.

There are several different conventional technologies for sensing NO gas for medical breath analysis applications. In laser detection, a laser may be tuned to a frequency which is selectively absorbed by NO. A photo detector then detects the transmission of laser light through a sample column, the degree of absorption by the gas being related to NO concentration. NO may also be detected by such methods as chemiluminescence, and other optical detection methods. See, for example, U.S. Pat. No. 6,038,913 entitled "Device for determining the levels of NO in exhaled air"; US Published Application No. 2003-0134,427, entitled "Method and apparatus for determining gas concentration", and US Published Application No. 2004-0017,570 entitled "Device and system for the quantification of breath gases", each of which is incorporated by reference. However, each of the conventional NO detection strategies suffer limitations in equipment size, weight, cost and/or operational complexity that limit their use for a low-cost, patent-portable.

SUMMARY

Embodiments having aspects of the invention provide sensors and detection systems suitable for measuring analytes, such as biomolecule, organic and inorganic species, including environmentally and medically relevant volatiles and gases, such as NO, NO2, CO2, NH3, H2, CO and the like. Certain embodiments of nanostructured sensor systems are configured for measurement of medically important gases in breath. Examples are described relating to the measurement of endogenous nitric oxide (NO) in breath, such as for the monitoring or diagnosis of asthma and other pulmonary conditions.

Particular embodiments for breath-species analysis and monitoring, and in particular the measurement of endogenous NO as a breath marker, bring the advantages of novel nanostructured electronic sensors to medical applications: (i) performance that matches or exceeds that of infrared technology; (ii) plug-and-play simplicity in a disposable package; (iii) the small size and low power consumption needed for portability and/or wireless integration; (iv) the ability to incorporate arrays of sensors on a single chip; and (v) an order of magnitude reduction in the cost of the sensor component.

Alternative embodiments having aspects of the invention include systems configured to measure more than one exhaled breath constituent, so as to provide monitoring and diagnosis based on patient-specific characteristics related to two or more of NO, CO2, H2O2 and other compounds. Likewise, the characteristics of the novel nanoelectronic sensors lend them to employment embodiments including sensor arrays, microprocessors and/or wireless transceivers, permitting convenient recordation and analysis of multivalent patient-specific measurement histories and/or remote patient monitoring by treatment personnel. See, for example, U.S. patent application Ser. No. 11/111,121 filed Apr. 20, 2005 (published 2006-0055,392) which is incorporated by reference.

Exemplary embodiments of sensor devices having aspects of the invention provide for detection of chemical, physiologic, or biomolecular species employing nanostructures as elements, both for use in gaseous and in liquid media, such as biological fluids, electrolytes, and the like. Real time electronic detection and monitoring and offers high sensitivity, is rapid and reversible, and has a large dynamic range. The output is digital so electronic filtering and post processing may be used to eliminate extraneous noise, if need be. Certain embodiments include multiplexed assays on a single sensor platform or chip.

Alternative embodiments having aspects of the invention are configured for detection of analytes employing nanostructured sensor elements configured as one or more alternative types of electronic devices, such as capacitive sensors, resistive sensors, impedance sensors, field effect transistor sensors, electrochemical sensors, and the like, or combinations thereof. Two or more such measurement strategies in a may be included in a sensor device so as to provide orthogonal measurements that increase accuracy and/or sensitivity. Embodiments may have functionalization groups or material associated with nanostructured elements to provide sensitive, selective analyte response.

Nanotubes were first reported in 1993 by S. Iijima and have been the subject of intense research since. Single walled nanotubes (SWNTs) are characterized by strong covalent bonding, a unique one-dimensional structure, and exceptionally high tensile strength, high resilience, metallic to semi-conducting electronic properties, high current carrying capacity, and extreme sensitivity to perturbations caused by charged species in proximity to the nanotube surface.

Although in the description herein a number of exemplary sensor embodiments are based on one or more carbon nanotubes, it is understood that other nanostructures known in the art may also be employed, e.g., semiconductor nanowires, various form of fullerenes, multiwall nanotubes, and the like, or combinations thereof. Elements based on nanostructures such carbon nanotubes (CNT) have been described for their unique electrical characteristics. Moreover, their sensitivity to environmental changes (charged molecules) can modulate the surface energies of the CNT and be used as a detector. The modulation of the CNT characteristic can be investigated electrically by building devices that incorporate the CNT (or CNT network) as an element of the device. This can be done as a gate transistor element or as a capacitive effect.

Certain exemplary embodiments having aspects of the invention include single-walled carbon nanotubes (SWNTs) as semiconducting or conducting elements. Such elements may comprise single or pluralities of discrete parallel NTs, e.g., in contact or electrically communicating with a device electrode. For many applications, however, it is advantageous to employ semiconducting or conducting elements comprising a generally planar network region of nanotubes (or other nanostructures) substantially randomly distributed adjacent a substrate, conductivity being maintained by interconnections between nanotubes.

Devices fabricated from random networks of SWNTs eliminates the problems of nanotube alignment and assembly, and conductivity variations, while maintaining the sensitivity of individual nanotubes For example, such devices are suitable for large-quantity fabrication on currently on 4-inch silicon wafers, each containing more than 20,000 active devices. These devices can be decorated with specific recognition layers to act as a transducer for the presence of the target analyte. Such networks may be made using chemical vapor deposition (CVD) and traditional lithography, by solvent suspension deposition, vacuum deposition, and the like.

See for example, U.S. Ser. No. 10/177,929 filed Jun. 21, 2002 (equivalent publication US 2007-0140,946), entitled "Dispersed Growth Of Nanotubes On A Substrate"; U.S. Pat. No. 6,894,359 entitled "Sensitivity Control for Nanotube Sensors"; U.S. Ser. No. 10/846,072 filed May 14, 2004 (published 2005-0184,641), entitled "Flexible Nanotube Transistors"; and L. Hu et al., *Percolation in Transparent and Conducting Carbon Nanotube Networks*, Nano Letters (2004), 4, 12, 2513-17, each of which application and publication is incorporated herein by reference.

The nanoscale elements can be fabricated into arrays of devices on a single chip for multiplex and multiparametric applications See for example, the following patent applications: U.S. Ser. No. 10/388,701 filed Mar. 14, 2003 (U.S. Pat. No. 6,905,655), entitled "Modification of Selectivity for Sensing for Nanostructure Device Arrays"; U.S. Ser. No. 10/656,898 filed Sep. 5, 2003 (published U2005-0279,987), entitled "Polymer Recognition Layers for Nanostructure Sensor Devices", U.S. Ser. No. 10/940,324 filed Sep. 13, 2004 (published 2005-0129,573), entitled "Carbon Dioxide Nanoelectronic Sensor"; and U.S. Ser. No. 11/111,121 filed Apr. 20, 2005 (published 2006-0055,392) entitled "Remotely Communicating, Battery-Powered Nanostructure Sensor Devices"; each of which is incorporated herein by reference.

Certain embodiments having aspects of the invention include a breath analyzer or medical monitor comprising:

at least a first nanoelectronic sensors, the sensor including a substrate; one or more nanostructures disposed over the substrate; one or more conducting elements in electrical communication with the nanostructure; and at least one material operatively associated with the first nanostructure, the at least one material configured to provide a sensitivity to a first analyte found in human breath;

a breath sampler configured to sample at least the exhaled breath of a patient, and in communication with the sensor; and a processing unit configured to receive a signal from the first sensor and to use the signal to measure the concentration of the first analyte, so as to provide information related to a medical state of the patient.

Certain breath analyzer embodiments may further comprise at least a second nanoelectronic sensor, which may be configured generally similar to the first sensor, and which includes recognition material configured to provide a sensitivity to a second analyte found in human breath; and wherein the processing unit is configured to receive a signal from the second sensor to use the signal to measure the concentration of the second analyte, so as to provide information related to a medical state of the patient. Certain breath analyzer embodiments may further comprise a output device to provide information related to the a medical state of the patient to a user.

The breath analyzer processing unit may be configured to compare the measurement of the first analyte with the measurement of the second analyte, so as to determine a relationship between the measurements indicative of a medical state of the patient. The analytes may include, for example, carbon dioxide (CO2), the second analyte may include nitric oxide or NO (detected directly or indirectly via a derivative, such as oxidatively-derived NO2), and the processing unit may be configured to determine a relationship of the measured concentrations of CO2 and NO in the sampled breath so as to provide an assessment of human airway inflammation of the patient.

In certain examples, the processing unit may be configured to determine an asthma status, and the output device to provide information related to the asthma status to a user. The breath analyzer may be substantially portable by a patient or other user, and configured to provide information related to the an asthma status to the patient or caretaker on a substantially real-time basis.

In certain embodiments, the one or more nanostructures comprise a network of carbon nanotubes, e.g., wherein at least a portion of the network is in contact with the one or more conducting elements. The conducting elements may include a source and a drain electrode separated from one another by a source-drain gap. In certain examples, the network of carbon nanotubes comprises nanotubes having a characteristic length substantially less than the source-drain gap, so that the nanotubes comprising the network substantially contact at most only one of the source and drain electrodes. In other examples, the characteristic length is substantially greater than the source-drain gap, so that a substantial portion of the nanotubes comprising the network contact both the source and the drain electrodes.

The breath analyzer sensors may further comprise a gate electrode; and the sensor signal may be indicative of a property of the nanostructure under the influence of a gate voltage. Alternatively, the sensor signal may be indicative of a capacitance property of the nanostructure. In certain embodiments, a breath monitor having aspects of the invention may be configured to measure one or more analytes such as $CO_2$, H2, CO, NO, $NO_2$, and $H_2O_2$. The breath monitor may be configured to delivery a continuing breath sample to either or both of the first sensor and the second sensor during at least a substantial portion of a patient exhalation; and the processing unit may be configured to determine a history of the concentration of either or both of the first analyte and the second analyte during the exhalation. The breath sampler may be configured to control pressure of the breath sample during the course of a patient exhalation.

Sensor with thin film functionalization/inhibition layer. One exemplary embodiment having aspects of the invention of a sensor device for detecting an analyte species in a gas or liquid sample medium, comprises (a) a substrate having a substrate surface; (b) one or more nanostructures disposed over the substrate surface; (c) one or more conducting elements in electrical communication with the nanostructure and configured to communicate with measurement circuitry; and (d) a functionalization/inhibition layer disposed so as to cover all or a portion of the one or more nanostructures; and to cover all or a portion of the substrate surface, the layer configured and composed so as to: (i) permit at least one interaction between the one or more nanostructures and the analyte species; so as to provide a detectable change in a property of the nanostructure in response to the presence of the analyte in the sample; and (ii) inhibit at least one interaction between the substrate surface and the sample medium, so as to prevent or reduce at least one interference response of the device which would be detectable by the measurement circuitry via the one or more conducting elements in the absence of the functionalization layer. The functionalization layer can also provide inhibition for exposed portions of electrical contacts.

The functionalization layer of the sensor device embodiment may be deposited by an ALD method (e.g., Al2O3 or ZrO2), and may comprise a substantially uniform layer. The layer may have a thickness between about 1 nm and about 100 nm. Alternative embodiments may be configured to have a sensitivity to different analytes, such as biomolecule, organic and inorganic species, including environmentally and medically relevant volatiles and gases, such as NO, NO2, CO2, NH3, H2, CO and the like. In an embodiment suitable for asthma monitoring, the embodiment may be configured to have a sensitivity to at least one of NO and NO2.

NO to NO2 conversion device. One exemplary embodiment having aspects of the invention of a NO to NO2 conversion device for converting endogenous NO to NO2 in an exhaled breath sample for subsequent measurement of the produced NO2, and comprises (a) an conduit including in communicating sequence: (i) an inlet portion configured to receive the breath sample under an input pressure sufficient to induce flow in the conduit, (ii) a conversion portion, and (iii) an outlet portion configured to dispense the breath sample following conversion; and (b) a conversion material disposed within the conversion portion, the conversion material comprising an active substance promoting conversion of NO to NO2 and a carrier material configured to support the active substance in contact with the breath sample, the conversion material configured to provide minimal pressure drop during sample flow across the conversion portion, to provide high conversion efficiency of NO to NO2, and to provide low loss of NO and/or NO2 via destruction or absorption.

The carrier material of the conversion device embodiment may comprise a fibrous material having a high surface/mass ratio and a high porosity, for example a loosely arranged quantity of quartz wool. The active substance may comprise a metal having catalytic activity for oxidizing NO in the presence of O2 to form NO2, for example Pt, Rh, Pd and the like or alloys thereof, which may be configured as fine particles dispersed upon the surface of the quartz wool fibers. The conversion device embodiment may further comprise a heating mechanism arranged adjacent the conduit and configured to maintain a selected elevated temperature of the conversion region. In one example, the heating mechanism includes a heating element, and a thermally conductive body in effective thermal communication with the heating element and at least the conversion region of the conduit. The conduit of the embodiment may further comprise a pre-heating region disposed in sequence upstream of the conversion region and in communication with the heating mechanism, so as to provide a selected elevation in temperature of the sample during flow through the pre-heating region. The heating mechanism of the embodiment may further comprise a feed-back temperature sensor and control circuitry configured maintain a selected temperature in the conversion region, for example of between about 100 C and about 350 C.

One method embodiment for dynamic sensor operation having aspects of the invention comprises (a) selectively exposing at least a portion of a sensor to a sample environment so that the sensor portion is exposed only intermittently and (b) dynamically sampling a response signal output from the sensor so as to determine the presence or concentration of the analyte of by analysis of the dynamically sampled signal. A number of alternative operational steps are described more particularly in the description below and the claims herein.

SUMMARY OF FIGURES

The following is a list and summary of the figures herein:

FIG. 9A-9B is a two-view schematic illustration (planar top view and side cross-section) illustrating an exemplary embodiment of a sensor device having aspects of the invention, and including a thin-film inhibition layer.

FIG. 18 is a plot illustrating sample-purge differential measurement methods.

FIG. 19 is a plot illustrating particular examples of sample-purge differential measurement comparisons between transistor characteristic curves.

FURTHER DESCRIPTION OF EMBODIMENTS

1. Nanosensor Architecture.

Figure 1:
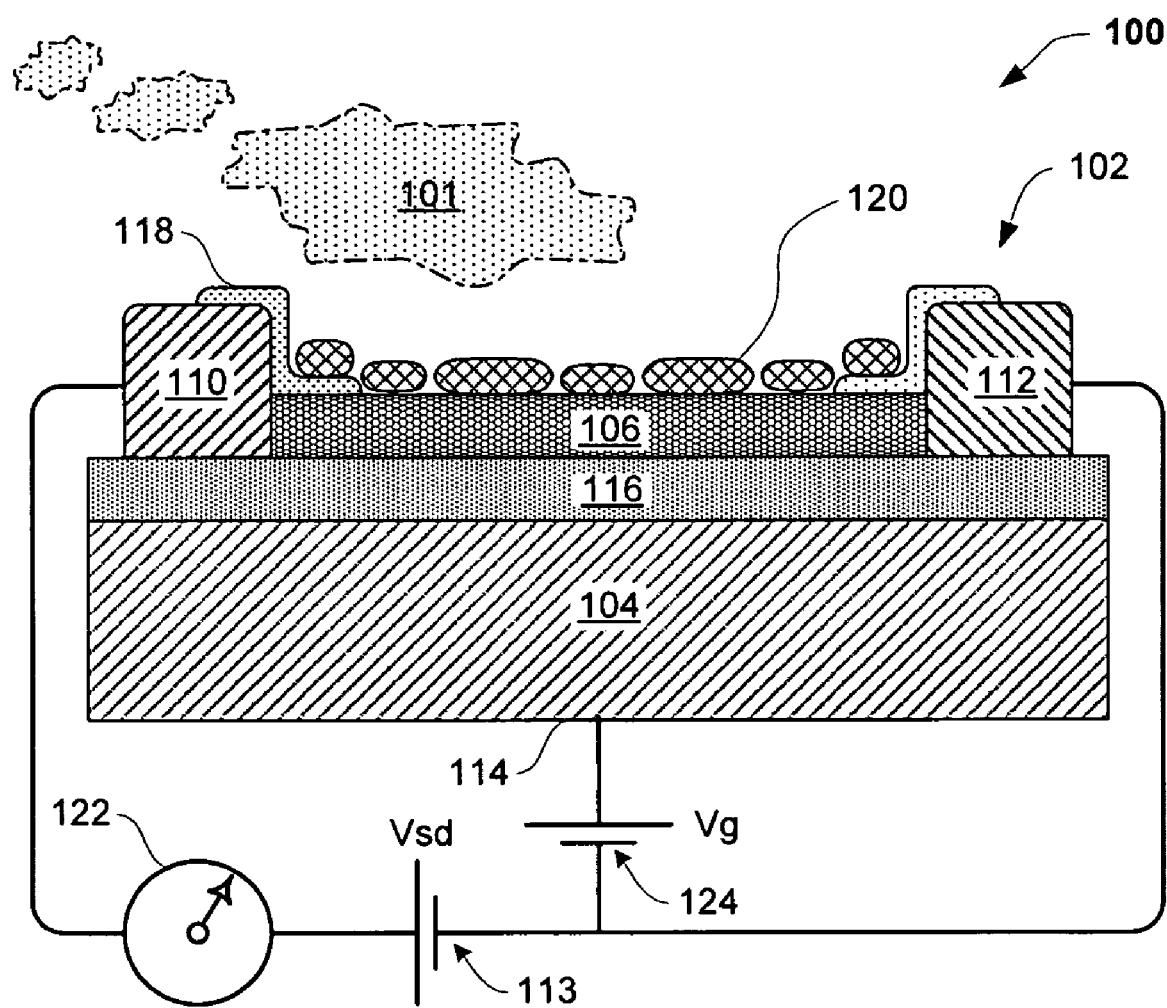
FIG. 1 is a cross-sectional diagram which illustrates an exemplary electronic sensing device for detecting an analyte, configured in this example as a NTFET.

FIG. 1. shows an exemplary electronic sensing device 100 having aspects of the invention, for detecting an analyte 101, such as biomolecule, organic and inorganic species, including environmentally and medically relevant volatiles and gases, such as NO, NO2, CO2, NH3, H2, H2O2, CO and the like. Sensing device 100 comprises a nanostructure sensor 102. Sensor 102 comprises a substrate 104, and a conducting channel or layer 106 comprising a nanostructure material, such as a nanotube or network of nanotubes, disposed on the substrate. The nanostructure material 106 may contact the substrate as shown, or in the alternative, may be spaced a distance away from the substrate, with or without a layer of intervening material.

In an embodiment of the invention, conducting channel 106 may comprise one or more carbon nanotubes. For example, conducting channel 106 may comprise a plurality of nanotubes forming a mesh, film or network. Certain exemplary embodiments having aspects of the invention include nanostructure elements which may be made using chemical vapor deposition (CVD) and traditional lithography, or may be deposited by other methods, such as solvent suspension deposition, AFM manipulation, and the like. Certain embodiments include one or more discrete nanotubes in electrical contact with one or more metal electrodes. A number of different arrangements of active nanostructures may be included without departing from the spirit of the invention.

At least two conductive elements or contacts 110, 112 may be disposed over the substrate and electrically connected to conducting channel 106 comprising a nanostructure material. Elements 110, 112 may comprise metal electrodes in contact with conducting channel 106. In the alternative, a conductive or semi-conducting material (not shown) may be interposed between contacts 110, 112 and conducting channel 106. Contacts 110, 112 may comprise source and drain electrodes, respectively, upon application of a source-drain voltage $V_{sd}$. The voltage or polarity of source 110 relative to drain 112 may be variable, e.g., the applied voltage may be DC, AC, pulsed, or variable. In an embodiment of the invention, the applied voltage is a DC voltage.

In the example of FIG. 1, the device 100 may be operated as a gate-controlled field effect transistor, with sensor 102 further comprising a gate electrode 114. Such a device is referred to herein as a nanotube field effect transistor or NTFET. Gate 114 may comprise a base portion of substrate 104, such as a doped-silicon wafer material isolated from contacts 110, 112 and channel 106 by a dielectric layer 116, so as to permit a capacitance to be created by an applied gate voltage $V_g$. For example, the substrate 104 may comprise a silicon back gate 114, isolated by a dielectric layer 116 comprising $SiO_2$.

Sensor 102 may further comprise a layer of inhibiting or passivation material 118 covering regions of the sensor, such as adjacent to the connections between the conductive elements 110, 112 and conducting channel 106, and/or covering all or portions of exposed substrate or electrode surfaces. The inhibiting material may be impermeable to at least one chemical species, such as to the analyte 101 or to environmental materials such as water or other solvents, oxygen, nitrogen, and the like. The inhibiting material 118 may comprise a passivation material as known in the art, such as silicon dioxide, aluminum oxide, silicon nitride, or other suitable material. Further details concerning the use of inhibiting materials in a NTFET are described in prior U.S. Pat. No. 6,894,359 entitled "Sensitivity Control For Nanotube Sensors" which is incorporated by reference herein.

Nanostructures such as carbon nanotubes may respond to a target analyte through charge transfer or other interaction between the device and the analyte (e.g., NO2, NH3 and the like). Alternatively, the conducting channel 106 (e.g., a carbon nanotube layer) may be functionalized to produce, regulate or enhance a sensitivity or selectivity for one or more target analytes 101, such as including a passivation or recognition layer.

The sensor functionalization or recognition material 120 may be selected for a specific application. In certain embodiments, a functionalization material 120 may be selected to interact with a targeted analyte 101 to cause a measurable change in electrical properties of nanosensor device 102. For example, the functionalization material 120 may cause an electron transfer to occur in the presence of analyte 101, or may influence local environment properties, such as pH and the like, so as to indirectly change device characteristics.

Alternatively or additionally, the functionalization or recognition material may induce electrically-measurable mechanical stresses or shape changes in the nanostructure channel 106 upon interaction with a target analyte. Sensitivity to an analyte or to multiple analytes may be provided or regulated by the association of a nanotube conducting channel 106 with an adjacent functionalization material 120. Specific examples of suitable functionalization materials are provided later in the specification. The functionalization material 120 may be disposed as a continuous or discontinuous layer on or adjacent to channel 106.

Alternatively or additionally, the recognition or functionalization material may enhance detection by selectively inhibiting reactions or processes between a sample medium and device structures (e.g., substrate and/or electrode surfaces) while permitting selective response (e.g., by charge transfer) of all or portions of the nanoparticles (e.g., nanotube network).

Device 100 may further comprise suitable circuitry in communication with sensor elements to perform electrical measurements. For example, a conventional power source may supply a source drain voltage $V_{sd}$ between contacts 110, 112. Measurements via the sensor device 100 may be carried out by circuitry represented schematically by meter 122 connected between contacts 110, 112. In embodiments including a gate electrode 114, a conventional power source 124 may be connected to provide a selected or controllable gate voltage $V_g$. Device 100 may include one or more electrical supplies and/or a signal control and processing unit (not shown) as known in the art, in communication with the sensor 102.

Figure 2:
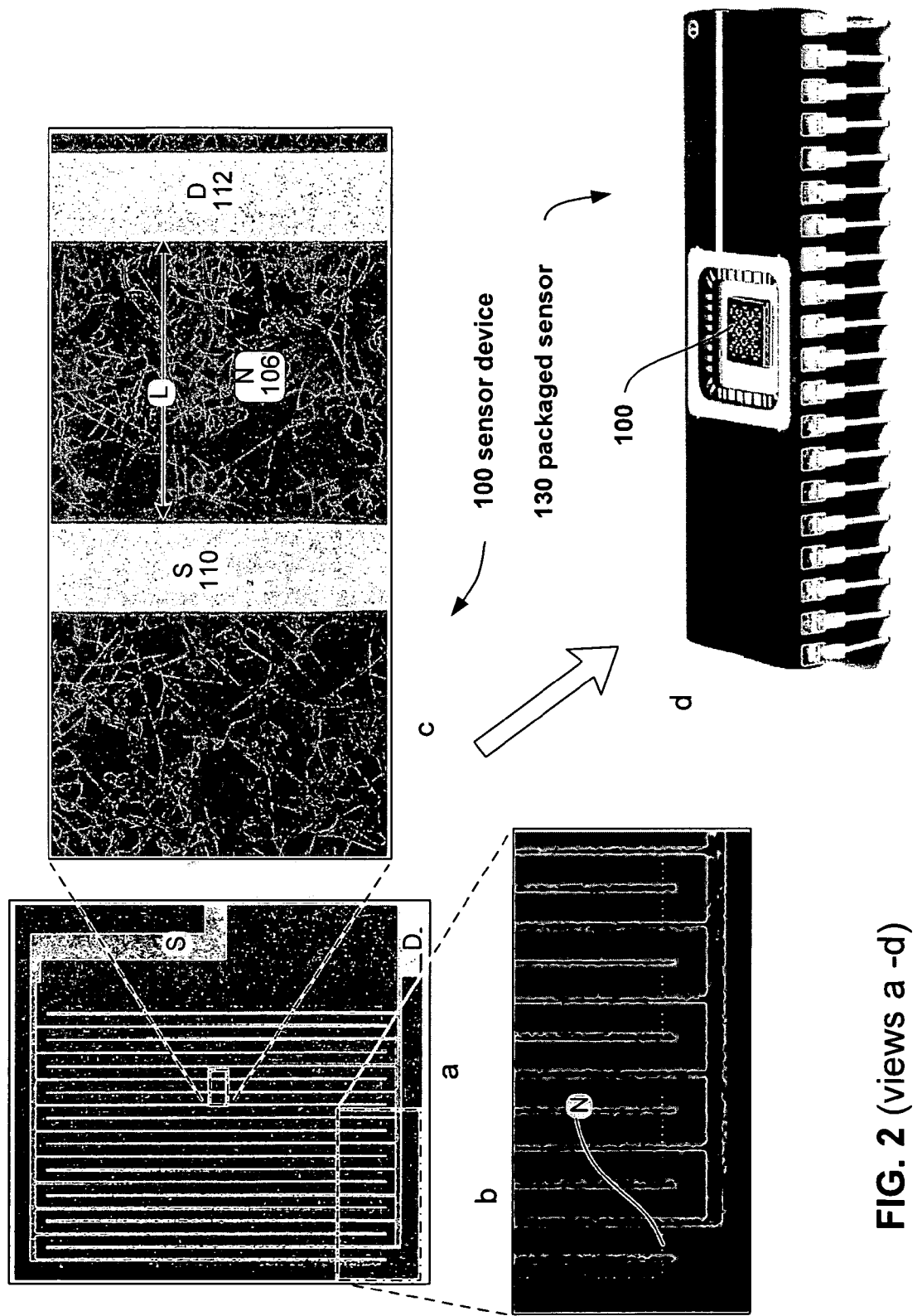
FIG. 2 are photographic views of a sensor system such as shown in FIG. 1, wherein views (a-c) include SEM images showing (a) showing the layout of interdigitated source and drain contacts S, D, (b) showing an enlarged detail of a nanotube network N and the contacts S, D, and (c) showing an enlarged detail of the margin of network N. View (d) shows an example of a sensor device mounted in a conventional electronic device package.

FIG. 2 (views a-d) are photographic views of an exemplary embodiment of a sensor system 100 having aspects of the invention and generally as shown in FIG. 1, wherein views (a-c) include SEM images showing (a) showing the layout of interdigitated source and drain contacts S 110 and D 112, (b) showing an enlarged detail of a nanotube network N 106 and the contacts S 110 and D 112, and (c) showing an enlarged detail of the margin of network N 106. View (d) shows an example of a sensor device 100 mounted in a conventional electronic device package 130. Note that the extent of a carbon nanotube network may be conveniently controlled by selective or masked removal of nanotubes, such as by oxidation of nanotubes from peripheral regions of the substrate 104 ("ashing"), by etching techniques, or the like.

Device 100 may be packaged in a conventional manner to conveniently permit connection to operating circuitry. FIG. 2, view (d) is a photograph of a sensor device 100 generally similar to that of views (a-c), fabricated on a die of a silicon wafer employing CVD methods, and mounted as a chip in a conventional 40 pin CERDIP package using wirebonding techniques. Device 100 may further comprise suitable circuitry in communication with sensor elements to perform electrical measurements. For example, a conventional power source may supply a source-drain voltage (Vsd) between contacts 110, 112. Measurements via the sensor device 100 may be carried out by circuitry represented schematically by meter 122 connected between contacts 110, 112. In embodiments including a gate electrode 114, a conventional power source 124 may be connected to provide a selected or controllable gate voltage (Vg). Device 100 may include one or more electrical supplies and/or a signal control.

2. Particular Sensor Elements.

Substrate. The substrate 104 may be insulating, or on the alternative, may comprise a layered structure, having a base 114 and a separate dielectric layer 116 disposed to isolate the contacts 110, 112 and channel 106 from the substrate base 114. The substrate 104 may comprise a rigid or flexible material, which may be conducting, semiconducting or dielectric. Substrate 104 may comprise a monolithic structure, or a multilayer or other composite structure having constituents of different properties and compositions. Suitable substrate materials may include quartz, alumina, polycrystalline silicon, III-V semiconductor compounds, and other suitable materials. Substrate materials may be selected to have particular useful properties, such as transparency, microporosity, magnetic properties, monocrystalline properties, polycrystalline or amorphous properties, or various combinations of these and other desired properties. For example, in an embodiment of the invention, the substrate 104 may comprise a silicon wafer doped so as to function as a back gate electrode 114. The wafer being coated with intermediate diffusion barrier of $Si_3N_4$ and an upper dielectric layer of $SiO_2$. Optionally, additional electronic elements may be integrated into the substrate for various purposes, such as thermistors, heating elements, integrated circuit elements or other elements.

In certain alternative embodiments, the substrate may comprise a flexible insulating polymer, optionally having an underlying gate conductor (such as a flexible conductive polymer composition), as described in U.S. application Ser. No. 10/846,072 (published 2005-0184,641) entitled "Flexible Nanotube Transistors", which application is incorporated by reference. In further alternative embodiments, the substrate may comprise a microporous material permitting suction to be applied across the substrate, e.g., porous alumina for vacuum deposition of a nanotube network channel 106 from suspension or solution, as described in U.S. Application No. 60/639,954, filed Dec. 28, 2004, entitled "Nanotube Network-On-Top Architecture For Biosensor", which application is incorporated by reference. Alternatively, the substrate may comprise a polymeric or organic material, which may be formed to a convenient shape or layered structure, such as a plastic sheet material (e.g., PET sheet).

Contacts or electrodes. In an NTFET example, the conductor or contacts 110, 112 used for the source and drain electrodes can be any of the conventional metals used in semiconductor industry, or may be selected from Au, Pd, Pt, Cr, Ni, ITO, W or other metallic material or alloy or mixture thereof. In the alternative, other conductive materials may be employed, such as conductive polymers, graphitic materials and the like. The contacts may comprise a multi-layer or composite of conductive materials, for example, to improve the adhesion of the metal to the substrate. In one example, electrical leads may be patterned on top of a nanotube network channel from titanium films about 10-30 nm thick capped with a gold layer about 100-120 nm thick. In another example, The dimension of the distance between source 110 and drain 112 may be selected to achieve desired characteristics for a particular application. It should be understood that one or more of each of a source and drain electrode may be arranged in an interdigitated or spaced-apart electrode array, permitting a comparative large area of nanostructure channel 106 having a comparatively small source-drain gap to be arranged compactly. Spacing of contacts may be selected to suit particular applications (see description below re nanostructure or nanotube networks and "statistical" conduction across nanotube networks). In one example, contacts may be spaced at about 1 micron to about 100 microns apart. In an array, different devices may be configured with different characteristic spacing.

The metal stack contains 10 nm of Ti and 100 nm of Au. An example of the I-Vg characteristics for device with 10 um spacing between source and drain electrodes is shown in FIG. 1.

Gate electrode 114 may comprise materials generally similar to contacts 110, 112. In the alternative, the gate electrode 114 may comprise a sublayer within substrate 104. Gate electrode 114 may comprise doped silicon, patterned metal, ITO, other conductive metal or non-metal material, or combinations thereof. Alternative forms of gate electrodes may be employed, such as a top gate, a gate effected via a conducting analyte carrier medium (e.g. an aqueous solution). Optionally, a device 102 may comprise such other electrodes as a counter electrode, a reference electrode, a pseudo-reference electrode, without departing from the spirit of the invention.

Conducting Channel Or Nanostructure Layer. Exemplary embodiments having aspects of the invention include sensor devices having at least one conducting channel 106 comprising one or more nanostructures. For example, conducting channel or layer 106 may comprise one or more single-wall carbon nanotubes, multiple-wall carbon nanotubes, nanowires, nanofibers, nanorods, nanospheres, or other suitable nanostructures. In addition, or in the alternative, conducting channel or layer 106 may comprise one or more nanostructures comprised of boron, boron nitride, and carbon boron nitride, silicon, germanium, gallium nitride, zinc oxide, indium phosphide, molybdenum disulphide, silver, or other suitable materials. Various suitable methods for manufacturing nanotubes and other nanostructures are known in the art, and any suitable method may be used.

Nanostructure Network Conducting Channel. In an embodiment of the invention, conducting channel or nanostructure layer 106 comprises an interconnected network of smaller nanostructures disposed to form a percolation layer, mesh, or film which provides at least one electrical conduction path between a source electrode 110 and a drain electrode 112.

In the exemplary embodiments described in detail herein, the conducting channel 106 comprises a randomly disposed network or film of single-walled carbon nanotubes (SWNTs), multi-walled carbon nanotubes (MWNTs), or mixtures thereof. In such a network of nanotubes, it is not necessary that any single nanoparticle extends entirely between the source and drain contacts. In operation the conductivity of channel 106 between source electrode 110 and drain electrode 112 may be maintained by interconnections, contacts or communications between adjacent nanostructures. Such networks of nanoparticles, such as nanotubes and the like, may be configured to be defect-tolerant, in that disruption of any particular conductive path may be compensated by remaining paths within the network. In an embodiment of the invention, nanostructure conducting channel 106 comprises one or more single-walled or multi-walled carbon nanotubes. The nanotubes may be arranged as clumps or bundles, or as distinct separated fibers. A useful network of nanotubes may be provided, for example, by distributing a dispersion of nanotubes over a substrate so as to be approximately planar and randomly oriented. For example, conducting channel 106 may comprise a network including a plurality of dispersed single wall carbon nanotubes (SWCNT), in which the nanotubes are oriented substantially randomly, non-parallel and separated with respect to one another (i.e., not clumped) as an interconnecting mesh disposed generally parallel to the substrate.

Electrical characteristics of the channel 106 may be optimized to suit a particular functionalization chemistry or other constituent of the sensor which effects conductivity, or to suit a desired range of analyte concentration. In preferred embodiments, the density or thickness of a nanotube network may be varied to provide a desired degree of conductivity between the source and drain electrodes. In the alternative, or in addition, the proportion of metallic or semiconducting nanotubes in the network may be selected to achieve a desired conductivity in the network. One advantage of using a nanostructure network architecture for the conducting channel 106 is that these factors may be varied to produce a conducting network having a selected margin above (or below) the percolation limit, permitting convenient optimization of device characteristics. For example, a NT network channel may be formed to be slightly below the percolation limit for the uncoated network, and modified by deposition of a conducting recognition material, such as Pd, to result in a functionalized channel of desired conductivity.

In addition, a conducting channel 106 comprising a generally random dispersion of individual nanoparticles advantageously permits a "statistical," rather than a "localized" approach to nanostructure device fabrication, which may be more amenable to demanding mass production techniques. In the "statistical" approach, electrical contacts can be placed anywhere on the dispersion of individual nanostructures to form devices, without a specific correspondence between electrode position and any particular nanoparticle position. The random dispersion of nanoparticles ensures that any two or more electrodes placed thereon can form a complete electrical circuit with functioning nanostructures providing the connection. By distributing a large plurality of randomly oriented nanotubes in a dispersion over (or under) an electrode array, uniform electrical properties in the individual devices can be assured with higher yields and faster processing than is possible using the prior art approach of controlled placement or growth of individual nanotubes or other nanostructures. Note that in this approach, in a source-drain example device, conduction across the film between source and drain may be a function of nanotube-to-nanotube charge transmission, in which substantially none of the nanotubes span between source and drain contacts.

Carbon nanotubes are known to exhibit either metallic or semiconductor properties, depending on the particular graphitic lattice orientation. Various methods may be employed to select a desired composition of nanotubes for a nanostructure layer 106 of a nanosensor device 102. For example, a plurality of generally similar nanotube devices may be fabricated in a parallel mass production process, such as an array of device dies disposed on a silicon wafer. Each of the plurality of devices will exhibit an electrical characteristic with a statistically predictable range of characteristics, due to differing metallic or semiconductor composition of each devices conducting layer 106. The fabricated dies may be individually tested, such as by automated or semi-automated pin probe test rigs. Dies exhibiting a selected electrical behavior or range of behavior may be marked and selected for further processing and use, and any non-conforming dies may be culled, or otherwise processed for other uses.

In the alternative, a network of nanostructures for conducting channel 106 may be constructed from preprocessed source nanotube material which includes a selected composition of metallic versus semiconductor properties (e.g., solely semiconductor nanotubes). Alternatively, the nanotube layer may be formed of an arbitrary mixture of nanotube composition, and the layer subsequently treated to selectively remove, oxidize, disconnect or deactivate all or a portion of the metallic nanotubes, e.g. by ohmic heating, so as to leave a conducting channel of selected properties (e.g., solely semiconductor nanotubes). The latter approach may be used advantageously where the nanotube layer 2 is formed directly upon the substrate 1, for example by catalyst initiated CVD.

Network Formation (vapor deposition example). Nanostructure networks may be formed by various suitable methods. One suitable approach may comprise forming an interconnecting network of single-wall carbon nanotubes directly upon the substrate, such as by reacting vapors in the presence of a catalyst or growth promoter disposed upon the substrate. For example, single-walled nanotube networks can be grown on silicon or other substrates by chemical vapor deposition from iron-containing catalyst nanoparticles with methane/hydrogen gas mixture at about 900 degree C. Advantageously, the use of highly dispersed catalyst or growth-promoter for nanostructures permits a network of nanotubes of controlled diameter and wall structure to be formed in a substantially random and unclumped orientation with respect to one another, distributed substantially evenly at a selected mean density over a selected portion of the substrate. The particle size distribution may be selected to promote the growth of particular nanotube characteristics, such as tube diameter, number of walls (single or multi-walled), conductivity, or other characteristics. Other catalyst materials and gas mixtures can be used to grow nanotubes on substrates, and other electrode materials and nanostructure configurations and are disclosed in U.S. application Ser. No. 10/099,664, filed Mar. 15, 2002 entitled "Modification Of Selectivity For Sensing For Nanostructure Sensing Device Arrays", and in U.S. application Ser. No. 10/177,929 (equivalent to published 2007-0140946) entitled "Dispersed Growth Of Nanotubes On A Substrate", both of which applications are incorporated by reference.

Network Formation (solution/suspension deposition example). In an alternative, conducting layer 106 comprising an interconnecting network of nanostructures may be formed by deposition from a solution or suspension of nanostructures, such as a solution of dispersed carbon nanotubes. Such methods as spin coating, spray deposition, dip coating and ink-jet printing may be employed to deposit the solution or suspension of nanostructures. Yet another suitable approach may comprise forming a nanotube network by suction deposition on a porous substrate or membrane, as described L. Hu et al., *Percolation in Transparent and Conducting Carbon Nanotube Networks*, Nano Letters (2004), 4, 12, 2513-17, which is incorporated by reference. The network thus formed may be used as a conducting channel either attached to its deposition membrane, or after being separated from the deposition membrane using a method such as membrane dissolution or transfer bonding. Although solution/suspension deposition is suitable to polymer and flexible substrates, it may be applied to substrates comprising inorganic and rigid materials, such as ceramic, quartz, silicon, and the like.

Figure 3:
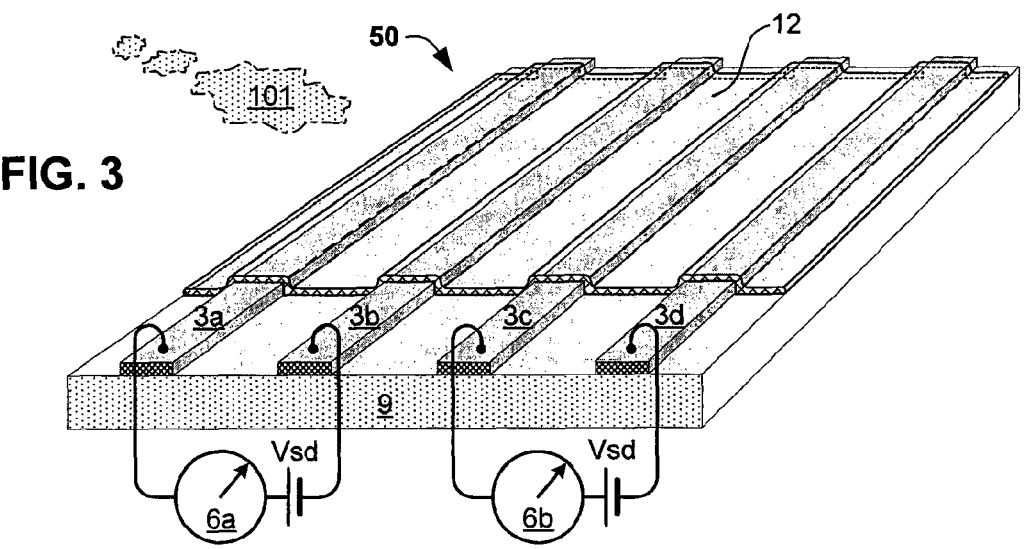
FIG. 3 shows an exemplary embodiment of a sensor device 50 having aspects of the invention and including a nanotube networks fabricated by deposition of a solution/suspension of nanotubes upon a substrate.

FIG. 3 shows an alternative exemplary embodiment of a sensor device 50 having aspects of the invention, for detecting an analyte 101, such as biomolecule, organic and inorganic species, including environmentally and medically relevant volatiles and gases, such as NO, $NO_2$, $CO_2$, $NH_3$, $H_2$, $H_2O_2$, CO and the like. Sensor device 50 includes a nanotube networks fabricated by deposition of a solution or dispersion of nanotubes upon a substrate 9 to form a nanotube film 12.

In an exemplary embodiment shown in FIG. 3, the nanotubes (or other nanostructures) are dispersed in a volatile solvent which evaporates following deposition to leave the nanotubes configured as an open network 12. In this example, a desired pattern of electrode or contact material 3 may be deposited upon the substrate 9 prior to nanotube deposition (four contacts 3a-3d are shown). For example, substrates (e.g., polymer sheets such as PET, polystyrene, polycarbonate and the like) are commercially made having printable conductor material applied in a selected pattern (e.g., carbon, silver, gold, silver/silver chloride, mixtures and the like). A suitable flexible PET substrates with a pattern of printed conductive carbon traces may purchased from Conductive Technologies, Inc., of York, Pa., for example, a flexible PET substrate with screen-printed carbon paste electrodes, with spacing between the conductive traces of about 1 mm. A plurality of devices may conveniently be fabricated on a sheet of substrate material, and may subsequently be partitioned and packaged as desired, either as single sensor devices, or as arrays of sensors, and the like.

Multi-walled and single-walled carbon nanotubes (collectively "CNTs") may be used in pristine or purified condition to form interconnecting networks by deposition from a solution or suspension. However, in alternative exemplary embodiments having aspects of the invention, pre-functionalized nanotubes may be included, for example, where functionalization groups promote solubility in solvents (e.g., hydrophilic groups permitting aqueous suspension.

In one example, the nanotube network was formed from SWNTs which were functionalized by covalently bonded poly-(m-aminobenzene sulfonic acid ("PABS"). A suitable nanotube composite material ("SWNT-PABS") may be obtained from Carbon Solutions, Inc. of Riverside, Calif. in the form of a dry powder. A variety of alternative functionalization carbon nanotube species may be included, such as conductive polymeric materials, polyaniline (PANI), polypyrrole, polyaniline derivatives, and the alternative materials described in TABLE 1 below.

A suitable aqueous deposition solution may be made by suspending SWNT-PABS powder in water (preferably at a concentration of about 1 mg/mL), and ultrasonication may be employed to assist in making a homogeneous dispersion. The carbon nanotube dispersion may be sprayed with an air brush to coat the substrate. Preferably the deposition is done in several light coating steps with intermediate drying (for example on a hotplate with the temperature of about 55 to 75 degree C.). The film resistance may be measured between steps until the selected resistance is obtained (the measurement may be between printed traces, or may be by pin probes on the network coating. For example, the deposition may be continued until resistance with a half-inch pin probe spacing is about 15 K Ohm.

Figure 4:
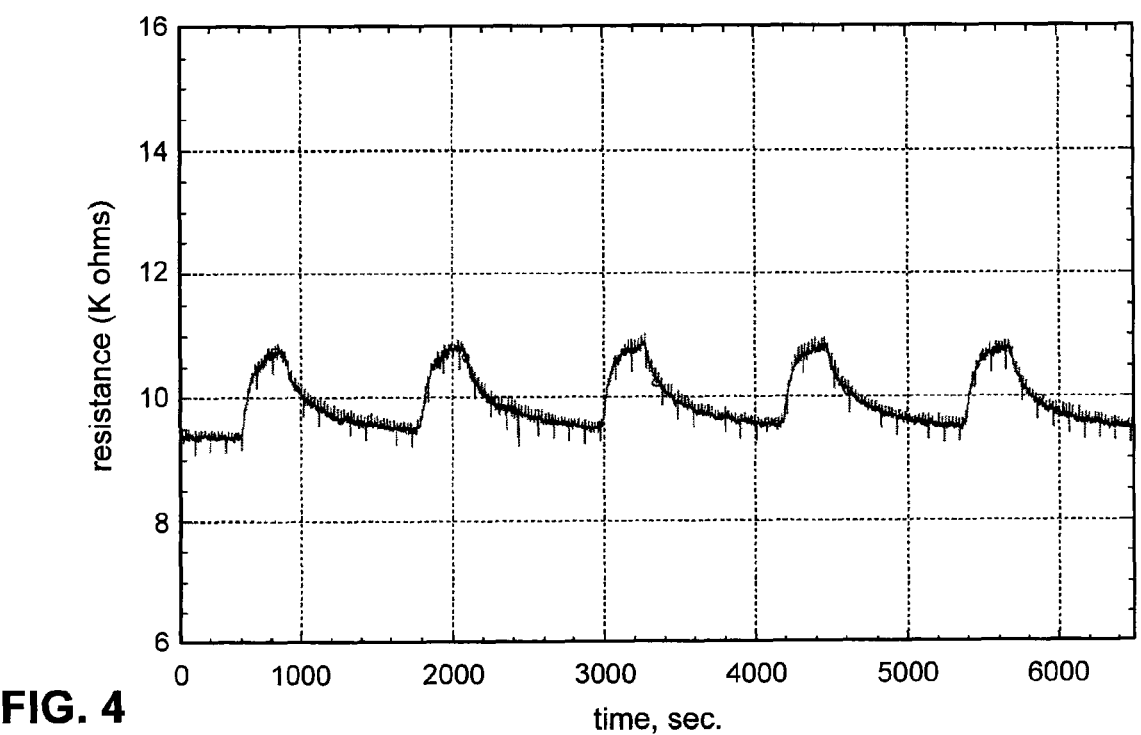
FIG. 4 shows the response of the sensor of FIG. 3 to repeated exposures of 50 ppm of ammonia.

FIG. 4 shows the response of a sensor such as shown in FIG. 3 sensor to repeated exposures and recovery at 50 ppm of ammonia (NH3). The response may be seen to be repeatable and consistent.

In an alternative embodiment, carboxylic acid functionalized CNTs (e.g., a suitable material is P2-SWNTs produced by Carbon Solutions, Inc of Riverside, CA) may be suspended in water by sonicating the mixture (e.g., for about 1 hour). The CNT suspension may be spray-deposited on a portion of a PET sheet substrate with pre-patterned traces until a sheet resistance about 1 k$\Omega$ was reached. For example, this may is performed using the moving head type BioDot instrument, such as CNT suspension drops (e.g, about 40 nl) may be cast on the electrode in one cycle of the instrument, and this may be repeated with small changes in spacing until the desired CNT amount and extent of coverage is obtained on the electrode. Alternatively, CNTs solution/suspension may be using a BioJet Plus instrument (moving head type) for application of a solution spray, such as with a shadow mask, to cover appropriate areas.

Further description of methods and devices including nanotube networks deposited from solution or suspension may be found in (a) U.S. Ser. No. 11/636,360 filed Dec. 8, 2006 (published 2008-0093226), entitled "Ammonia Nanosensors, and Environmental Control System"; (b) U.S. Ser. No. 11/274,747 filed Nov. 14, 2005 (published 2007-0208243), entitled "Nanoelectronic Glucose Sensors"; (c) U.S. application Ser. No. 10/846,072, (published 2005-0184, 641) entitled "Flexible Nanotube Transistors"; and (d) U.S. provisional application No. 60/937,256 filed Jun. 25, 2007 entitled "Nanoelectronic Electrochemical Test Device"; each of which is incorporated by reference.

Functionalization or Recognition Layer. Functionalization or recognition material 120 may be selected for a wide range of alternative chemical or biomolecular analytes. Examples include functionalization specific to gas analytes of industrial or medical importance, such as carbon dioxide as disclosed in application Ser. No. 10/940,324 filed Sep. 13, 2004 entitled "Carbon Dioxide Nanoelectronic Sensor", which is incorporated herein by reference. See also application Ser. No. 10/656,898 referenced hereinabove. Examples of functionalization materials specific to biomolecules, organisms, cell surface groups, biochemical species, and the like are disclosed in application U.S. application Ser. No. 10/345,783, filed Jan. 16, 2003, entitled "Electronic Sensing Of Biological And Chemical Agents Using Functionalized Nanostructures" (published 2003-0134433), and in application Ser. No. 10/704,066 referenced hereinabove, both of which applications are incorporated herein by reference. Additional examples of useful functionalization layers or materials may be found in 2007-0048,181 (Mar. 1, 2007)

Functionalization or recognition material 120 may comprise as little as a single compound, element, or molecule bonded to or adjacent to the nanostructure channel 106. In addition, or in the alternative, functionalization materials may comprise a mixture or multilayer assembly, or a complex species (e.g., including both synthetic components and naturally occurring biomaterials). Functionalization material 120 may comprise more than one material and/or more than one layer of material, also referred to as "functionalization material", "functionalization layer" or "functionalization".

For increasing selectivity and sensitivity to an analyte (e.g., NO2) functionalization material 120 may comprise polyethyleneimine (PEI), polyamidoamine (PAMAM), Polydi(carbazol-3-yl)phenylamine, nylon or poly(N-isopropylacylamide) (PNIMAM).

The functionalization layer can be constructed using certain polymeric materials such as polyethylene glycol, poly (vinyl alcohol) and polysaccharides, including various starches as well as their components amylose and amylopectin. For example, a suitable reaction layer may be formed from a combination of PEI or similar polymer with a starch polymer. Other suitable materials for the functionalization layer may include, for example, metals, metal oxides, and metal hydroxides. In addition, a metallic functionalization layer may be combined with a polymeric functionalization layer.

Materials in the functionalization layer may be deposited on the NTFET using various different methods, depending on the material to be deposited. For example, inorganic materials, such as sodium carbonate, may be deposited by drop casting from 1 mM solution in light alcohols. The functionalized sensor may then be dried by blowing with nitrogen or other suitable drying agent. Polymeric materials may be deposited by dip coating. A typical procedure may involve soaking of the chip with the carbon nanotube device in 10% polymeric solution in water for 24 hours, rinsing with water several times, and blowing the chip dry with nitrogen. Polymers which are not soluble in aqueous solutions may be spin coated on the chip from their solutions in organic solvents. Values of polymer concentrations and the spin coater's rotation speeds may be optimized for each polymer.

Alternative materials for layer 120 may include, for example, those shown in TABLE 1. Such materials may be included in sensors such as are describe herein without departing from the spirit of the invention:

TABLE 1

Examples of alternative functionalization and/or recognition materials

| | |
|---|---|
| Polyacrylic acid | Polyurethane resin |
| Poly(acrylic acid-co-isooctylacrylate) | Polycarbazole |
| poly(ethylene imine), "PEI" | poly(sulfone) |
| poly(4-vinylphenol) | poly(vinyl acetate) |
| poly(alkyl methacrylate) | poly(vinyl alcohol) |
| poly(a-methylstyrene) | poly(vinyl butyral) |
| poly(caprolactone) | polyacrylamide |
| poly(carbonate bisphenol A) | polyacrylonitrile |
| poly(dimethylsiloxane) | polyaniline |
| poly(ethylene glycol) | polybutadiene |
| poly(ethylene oxide) | polycarbonate |
| poly(ethylenimine) | polyethylene |
| poly(methyl vinyl ether-co-maleic anhydride) | polyoxyethylene |
| poly(N-vinylpyrrolidone) | polypyrrole |
| poly(propylene) | polytetrafluoroethylene |
| poly(styrene) | polythiophene |
| polyvinyl-methyl-amine | Polyvinyl pyridine |
| polyaminostyrene | |
| chitosan | chitosan HCL |
| polyallylamine | polyallylamine HCL |
| poly(diallylamine) | poly(diallylamine) HCL |
| poly(entylene-co-vinyl acetate), ~82% ethylene | poly-(m-aminobenzene sulfonic acid), "PABS" |
| poly(styrene-co-allyl alcohol), ~5.7% hydroxyl | poly(vinyl chloride-co-vinyl acetate), ~10% vinyl acetate |
| poly(styrene-co-maleic anhydride), ~50% styrene | poly(vinylidene chloride-co-acrylonitrile), ~80% vinylidene chloride |
| metalloporphyrin (M-porph) | Poly-L-lysine |
| Alpha-fetoprotein Profile Four (AFP4) | glycerol |
| Poly methyl methacrylate (PMMA) | polyglycerol |
| Nafion NR 50 | Triton 100 and similar surfactants or amphiphilic species |
| metal coatings and nanoparticles, and alloys or mixtures of these: | Fe, V, Au, Pt, Pd, Ag, Ni, Ti, Cr, Cu, Mg, Al, Co,, Zn, Mo, Rh, Sn, W, Pb, Ir, Ru, Os |
| inorganic coatings and/or nanoparticles: | |
| $V_2O_5$ | $WO_3$ |
| $Cu(SO_4)$ | Boric/Boronic acid |
| ZnO | Boron Trichloride |
| $Al_2O_3$ | $ZrO_2$ |
| $Fe_2O_3$ | $CaCl_2$ |

Materials in the functionalization layer may be deposited on the NTFET using various different methods, depending on the material to be deposited. It should be understood that mixtures, alloys and composites of the materials may also be included. For many materials, ALD methodology is known which is suitable for depositing thin, uniform layers or coatings, which may be controlled to deposit on selected portions of a device, and which may be employed to produce mixtures or multi-layer coatings also. See, for example, U.S. Ser. No. 11/588,845 filed Oct. 26, 2006 (published 2008-0021339), entitled "Anesthesia Monitor, Capacitance Nanosensors and Dynamic Sensor Sampling Method", which is incorporated by reference.

Other methods may be employed. For example, inorganic materials, such as sodium carbonate, may be deposited by drop casting from 1 mM solution in light alcohols. The functionalized sensor may then be dried by blowing with nitrogen or other suitable drying agent. Polymeric materials may be deposited by dip coating. A typical procedure may involve soaking of the chip with the carbon nanotube device in 10% polymeric solution in water for 24 hours, rinsing with water several times, and blowing the chip dry with nitrogen. Polymers which are not soluble in aqueous solutions may be spin coated on the chip from their solutions in organic solvents. Values of polymer concentrations and the spin coater's rotation speeds may be optimized for each polymer.

Alternative Substrate or Device elements. Optionally, the substrate may include integrated temperature management elements such as a microfabricated heater structure, a Peltier type micro-cooler, thermal isolation bridges, thermister/microprocessor feedback controller, and the like. Note that thermal control may be used to achieve a wide variety of sensor performance goals. For example, temperature control can be used to increase response rate by accelerate analyte reactions; to improve sensor recovery time by evaporating prior analyte or reaction products; by optimizing reactions (e.g., DNA hybridization, stringency controls); by evaporating condensed media vapors; and the like. Likewise, other advantageous processing, power supply or support circuitry may be integrated on a sensor chip.

See U.S. application Ser. No. 10/655,529 (published 2007-0045,756) entitled "Improved Sensor Device With Heated Nanostructure", which is incorporated by reference. See also suitable micromachining and/or etching techniques are described in A. Tserepi et al, "Fabrication of suspended thermally insulating membranes using front-side micromachining of the Si substrate: characterization of the etching process", J. of Micromech, and Microeng, Vol. 13, p. 323-329 (2003); C. Tsamis et al, "Fabrication of suspended porous silicon micro-hotplates for thermal sensor applications", Physica Status Solidi (a), Vol. 197 (2), p. 539-543 (2003); and A. Tserepi et al, "Dry etching of Porous Silicon in High Density Plasmas", Physica Status Solidi (a), Vol. 197 (1), p. 163-167 (2003), each of which publication is incorporated by reference herein.

Optionally, the substrate may include protective and surface conditioning layers. For example a diffusion barrier may be included to prevent contamination of a substrate, such as doped silicon, by metallic catalysts or other substances introduced during fabrication steps. See U.S. application Ser. No. 11/354,561 (published 2006-0263,255) entitled "Nanoelectronic Sensor System And Hydrogen-Sensitive Functionalization"; which application is incorporated by reference.

3. Measurement Systems.

The electronic circuitry described in this example is by way of illustration, and a wide range of alternative measurement circuits may be employed without departing from the spirit of the invention. Embodiments of an electronic sensor device having aspects of the invention may include an electrical circuit configured to measure one or more properties of the nanosensor 120, such as measuring an electrical property via the conducting elements 110, 112. For example, a transistor sensor may be controllably scanned through a selected range of gate voltages, the voltages compared to corresponding measured sensor current flow (generally referred to herein as an I-$V_g$ curve or scan). Such an I-$V_g$ scan may be through any selected gate voltage range and at one or more selected source-drain potentials. The $V_g$ range is typically selected from at least device "on" voltage through at least the device "off" voltage. The scan can be either with increasing $V_g$, decreasing $V_g$, or both, and may be cycled positive or negative at any selected frequency. See, for example, dynamic sampling and other measurement methods described in U.S. applications No. 60/922,642 filed Apr. 10, 2007 entitled "Ammonia Nanosensors, and Environmental Control System"; Ser. No. 11/636,630 (published 2007-0079498) entitled "Ammonia Nanosensors, and Environmental Control System"; Ser. No. 11/588,845 entitled "Anesthesia Monitor, Capacitance Nanosensors and Dynamic Sensor Sampling Method"; and Ser. No. 11/437,275 (published 2007-0048,180) entitled "Nanoelectronic Breath Analyzer and Asthma Monitor"; each of which is incorporated by reference.

In addition to the transconductance/NTFET example of FIG. 1, it should be understood that alternative embodiments of an electronic sensing device for detecting an analyte having aspects of the invention may include sensors configured with other architectures and for measurement of other properties. Any suitable electrical or magnetic property may provide the basis for sensor sensitivity, for example, electrical resistance, electrical conductance, current, voltage, capacitance, impedance, inductance, transistor on current, transistor off current, and/or transistor threshold voltage. In the alternative, or in addition, sensitivity may be based on a measurements including a combination of properties, relationships between different properties, or the variation of one or more properties over time. For example, a sensor embodiment may include circuitry and elements configured and optimized for measurement of capacitance relative to a nanostructured sensor element, for example, the response of the capacitance of a functionalized nanotube network to interaction with an analyte of interest.

Note that a sensor system may include suitable circuitry to perform measurement of more than one property of a single electronic sensor device. For example, a sensor device configured as a FET may have (a) resistance or conductance measurements performed across the conductive channel element, (b) channel resistance or conductance may be measured under the influence of constant or variable gate voltage, (c) a capacitance or impedance of the device measured relative to the gate electrode and the conductive channel, (d) time integrated characteristics such as hysterisis, phase shifts, recovery behavior, or like properties or combinations thereof. The use of multiple measurement strategies using a single sensor on a real-time basis allows increased accuracy, sensitivity and selectivity.

From such measurements, and from derived properties such as hysteresis, time constants, phase shifts, or scan rate/frequency dependence, correlations may be determined with target detection or concentration. The electronic sensor device may include or be coupled with a suitable microprocessor or other computer device as known in the art, which may be suitably programmed to carry out the measurement methods and analyze the resultant signals. Those skilled in the art will appreciate that other electrical or magnetic properties may also be measured as a basis for sensitivity. Accordingly, the embodiments disclosed herein are not meant to restrict the types of device properties that can be measured.

Optionally, the measurement circuitry may be configured so as to provide compensation for such factors as temperature and pressure and humidity. See U.S. application Ser. No. 11/111,121 (published 2005-0245,836) entitled "Remotely communicating, battery-powered nanostructure sensor devices"; which is incorporated by reference.

4. Sensor Arrays.

A plurality of sensor devices 102 may be conveniently arranged as an array embodiment, the array being configured to provide for a number of advantageous measurement alternatives, as described in the patent applications incorporated by reference above. A number of different measurement methods and benefits are enabled by a sensor array according to the invention, for example:

a) multiple analytes detected by a plurality of specifically functionalized sensors,
b) increased precision and dynamic range by a plurality of sensors each of which is optimized for a different range,
c) increased analyte specificity and flexibility by detecting a characteristic "profile" of responses of a target analyte to a plurality of differently-functionalized sensors,
d) self calibration systems and isolated reference sensors,
e) multiple-use array having a plurality of deployable one-time-use sensor sub-units, or
f). ultra-low-cost, direct-digital-output sensor arrays, including a plurality of sensors, each producing a binary signal, and collectively having a range of response thresholds covering a selected analyte concentration range.

The nanoelectronic sensors having aspects of the invention are inherently suitable to array configurations, such as may be employed in the multi-analyte integrated breath analysis system described herein. These sensors and sensor arrays can be fabricated by a range of known manufacturing technologies (see U.S. patent application Ser. No. 10/846,072 entitled "Flexible Nanotube Transistors" which is incorporated herein). One preferred approach is to use the wafer processing technology developed for the semiconductor electronics industry. This approach not only permits many sensors to be made on as single chip, but permits sensors of different functional types and different architectures to be produced simultaneously on a common substrate, using appropriate photo-lithographic techniques, masking, controlled etching, micro-machining, vapor deposition, "ink jet" type chemical application and circuit printing, and the like, to produce the elements of the various sensor devices and associated circuitry.

5. Direct NO Sensor Examples.

Figure 5:
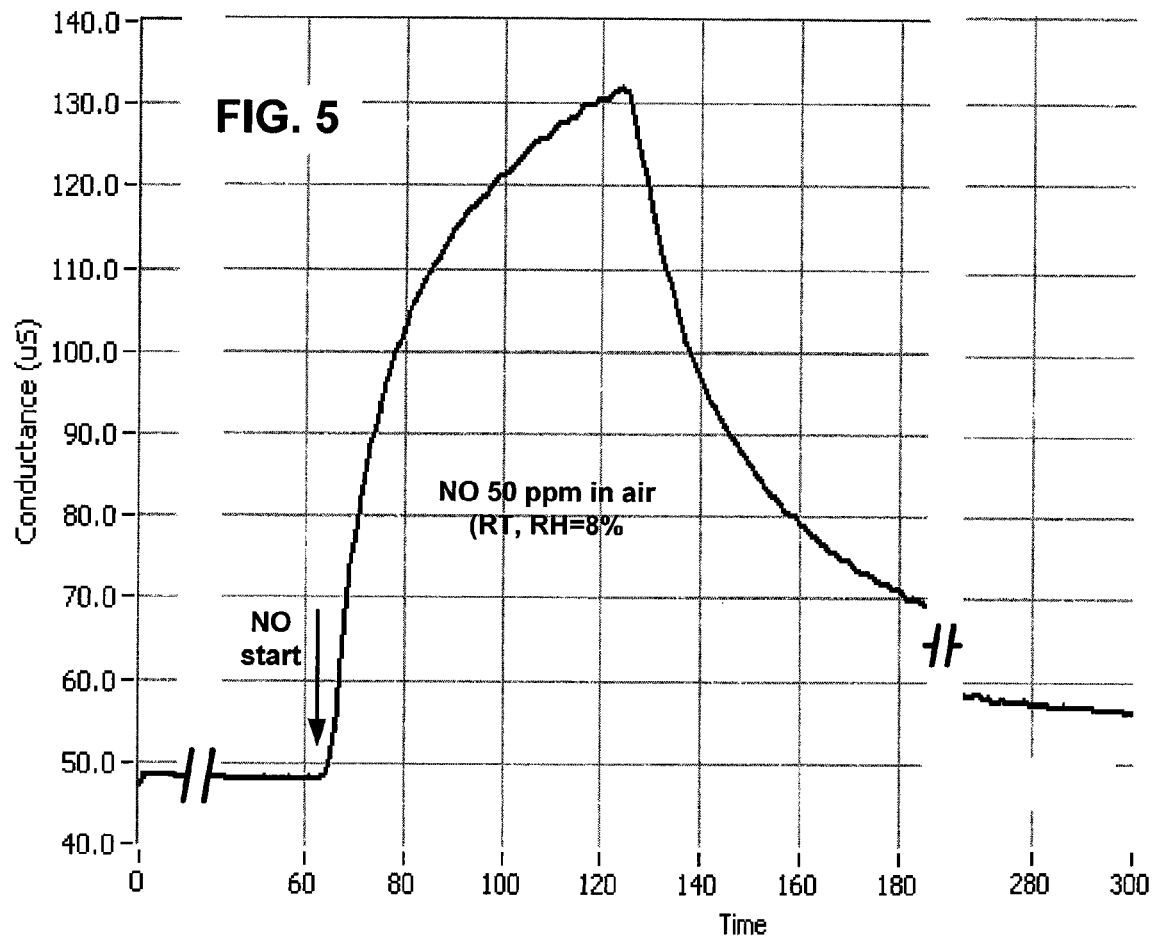
FIG. 5 shows a plot of the response of an exemplary nanostructure sensor, having aspects of the invention to a short exposure to NO in air.

FIG. 5 shows a plot of the response of an exemplary nanostructure sensor, having aspects of the invention to a short exposure to NO in air at 50 ppm concentration (room temperature and an relative humidity of 8%). The results shown are for the response to nitric oxide of the functionalized NTFET devices as packaged devices (See packaged device 100' in FIG. 2d). In these measurements packaged devices were tested in a flow cell at controlled humidity and at a selected concentration of NO gas balanced with air. Functionalized NTFET devices have showed reliable responses to NO gas in air at ambient conditions as low as 50 ppm. The degree of response indicates that much lower thresholds are possible, e.g. in the low ppb regime.

Figure 6:
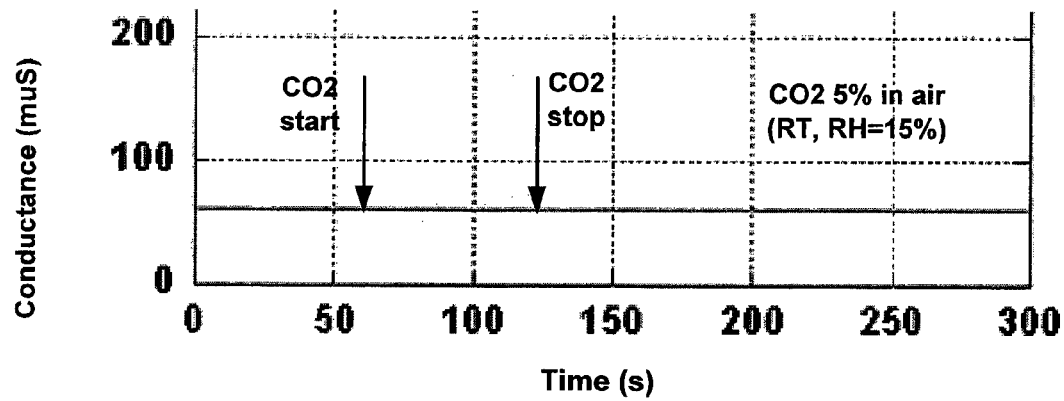
FIG. 6 shows a plot demonstrating that the NO sensor device of FIG. 4 has little or no cross-sensitivity when exposed to a CO2 concentration representative of breath.

As shown in FIG. 6, the NO sensor device shows little or no cross sensitivity to CO2, an interferant in breath. In this case, the device was exposed (room temperature and an relative humidity of 8%) to a CO2 concentration of 5%, representative of exhaled human breath.

In this example, the sensor platform employed includes a field effect transistor (FET) made from semiconducting single-walled carbon nanotubes (NTFETs) (see FIG. 1). A functionalize NTFET devices have been found to be specific to nitric oxide gas. The functionalization layer has two main functions: 1) it selectively recognizes nitric oxide molecules and 2) upon the binding of NO it generates an amplified signal that is transferred to the carbon nanotube transducer. Thus the surface modification provides the sensitivity and the selectivity of the NTFET for NO quantification at the low concentration levels.

The functionalization approach relies on the ability of basic inorganic compounds and organic polymers, aromatic compounds, biological relevant molecular receptors with possible electron-donating functionalities to provide electrons to nanotubes, thus resulting in preferred doping of NTFETs. To this end, electropolymerization and/or deposition of suitable electroactive species is employed to form thin, stable, and reproducible films on carbon nanotube network. Moreover, the rate and extend of polymerization and thus the thickness and physicochemical properties of the resulting electrodeposited film, can be accurately controlled by careful monitoring of the electrochemical parameters.

A number of different functionalization materials may be included in NO detection sensors having aspects of the invention without departing from the spirit of the invention. Examples of materials that may be used for carbon nanotube surface modification include numerous metal complexes of porphyrins and phthalocyanines as well as conducting polymers, such as polyaniline and polypyrrole. The recognition of NOx molecules can be also achieved by using amino-containing polymers, i.e., poly(ethyleneimine), bis-amino terminated poly(ethylene glycol), as well as such aromatic compounds as (benzylamine, naphthalenemethylamine, calix[4] arenes, and the like). For further examples of NTFET functionalization materials may be included in NO sensors, see the discussion above regarding functionalization and recognition materials and TABLE 1.

6. NO2 Sensor Examples.

It should also be noted that alternative sensor embodiments for detection of NO may employ methods of oxidation of NO in a sample, without departing from the spirit of the invention. For example, NO may be oxidized to form $NO_2$, followed by detection of the resultant $NO_2$ using a sensor configured to have a sensitivity to $NO_2$. Various strategies may be employed, such as exposure of a breath sample to a catalyst in the presence of oxygen (e.g., in exhaled air), or by exposure to a suitable oxidizing compound, e.g., permanganate salts, perchlorate salts, various metallic oxides and the like. See for example, U.S. Ser. No. 11/437,275 (published 2007-0048, 180) entitled "Nanoelectronic Breath Analyzer and Asthma Monitor".

Also, US publication 2004-0133,116 entitled "Device and method for the quantitive determination of nitrogen oxides in exhaled air and application thereof" describes oxidation of NO to NO2 using permanganate salts or perchlorate salts applied to a catalyst support including zeolite, alumina or silica gel.

See additional description in of a particular NO to NO2 conversion device having aspects of the invention below with respect to FIG. 9

In one embodiment having aspects of the invention, inhaled air may be passed through a "scrubber" device to remove environmental NO (and/or any other selected substance, such as CO2, NOx and the like) prior to administration to a patient or test subject. During or after a collection of a subsequent exhaled air sample, the sample may be passed through an conversion device to oxidize all or a portion of the NO to NO2. Optionally, the exhaled sample may be passed through one or more filter or absorber devices to remove particulates, water vapor, atomized fluids, and/or gasses such as CO2 and the like.

Figure 7:
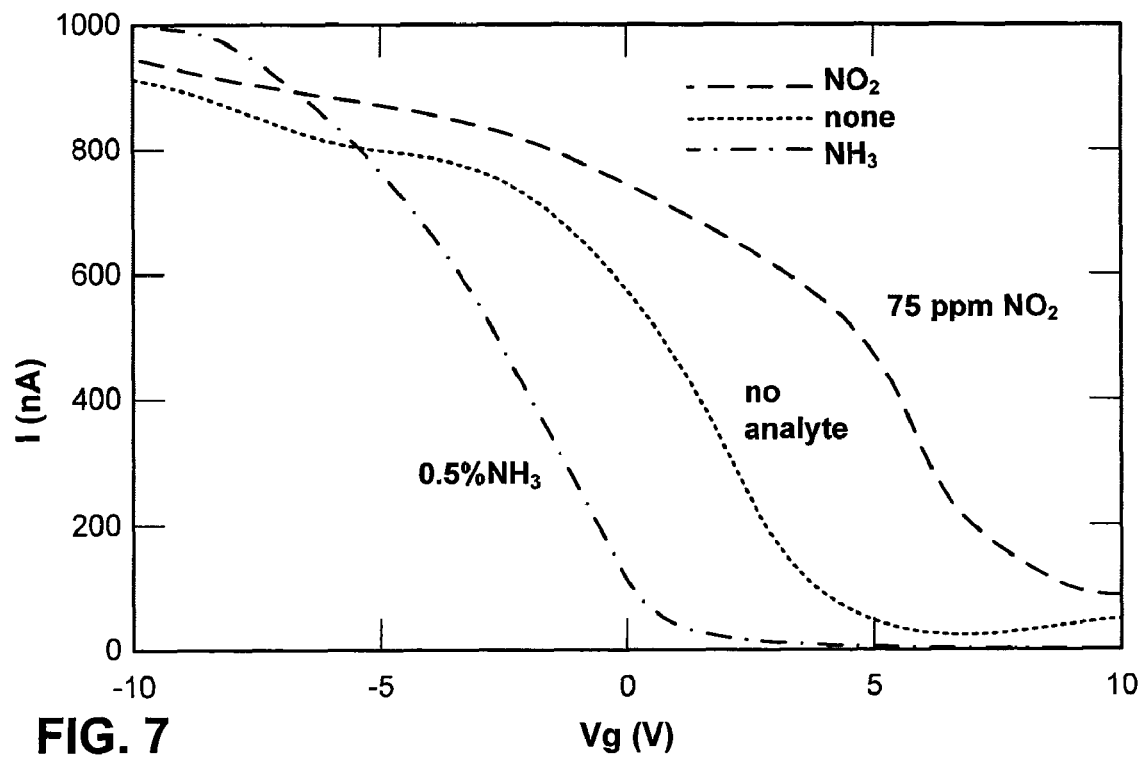
FIG. 7 illustrates the operation one exemplary embodiment having aspects of the invention, and the effect for an electron donating (NH3) and electron withdrawing (NO2) species on the NTFET transistor device characteristic.

FIG. 7 illustrates the operation one exemplary embodiment having aspects of the invention, and the effect for an electron donating (NH3) and electron withdrawing (NO2) species on the NTFET transistor device characteristic, believed to be the result of charge transfer between the molecular species and the carbon nanotubes. In this example, the NTFET devices were fabricated using SWNTs grown by chemical vapor deposition (CVD) on 200 nm of silicon dioxide on doped silicon from iron nanoparticles with methane/hydrogen gas mixture at 900° C. Electrical leads were patterned on top of the nanotubes from titanium films 35 nm thick capped with gold layers 5 nm thick, with a spacing of 0.75 μm between source and drain. The devices were contact-passivated with a liftoff-patterned SiO layer, which was extended over the leads and for several hundred nanometers on either side.

Upon exposure to gases, the transfer characteristics shifted left (for NH3) or right (for NO2), towards more negative or more positive gate voltages. These findings show that the exposed nanotube channel plays an essential role in the nanotube transistor. Without being limited by theory, these results may be due to charge transfer between the nanotubes and the analytes involving either electron donors (NH3) or acceptors (NO2). Such gas analyte doping is capable of modifying the device characteristics even when the contacts are covered.

Figure 8:
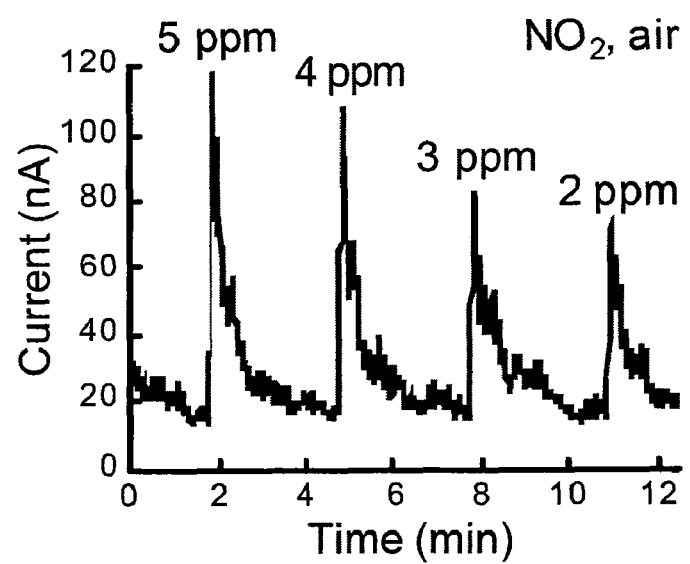
FIG. 8 shows the response of an exemplary NTFET embodiment having aspects of the invention and including PEI polymer recognition layer too four brief exposures to NO2 gas.

In an alternative exemplary embodiment having aspects of the invention, a nanotube device such as shown and described with respect to FIG. 1 may be employed, wherein the nanotube network may be coated with a thin polymer layer, such as poly(ethylene imine) ("PEI") (see layer 120). For example, the polymer layer may be about 10 nm thick. In this configuration, the device may be operated as an n-type FET. FIG. 8 shows the response of a PEI polymer-coated NTFET to four brief exposures to $NO_2$ gas.

It may also be operated in a resistive mode as a sensor, and exhibits an improved response to NH3, NO2, and H2. Surprisingly, functionalization of nanostructure devices by coating with PEI has been found to improve the response of the devices for some gases, such as NH3 and NO2, and induce a response to other gases, such as H2.

For further description, see (a) U.S. Ser. No. 10/656,898 filed Sep. 5, 2003 (published 2005-0279,987), entitled "Polymer Recognition Layers For Nanostructure Sensor Devices"; (b) A. Star, K. Bradley, J.-C. P. Gabriel, G. Grüner, "Nano-Electronic Sensors: Chemical Detection Using Carbon Nanotubes", Pol. Mater.: Sci. Eng. 89, pp 204 (2003); and (c) U.S. Ser. No. 11/259,414 filed Oct. 25, 2005 (published 2006-0228723) entitled "Systems And Method For Electronic Detection Of Biomolecules"; each of which is incorporated by reference.

7. Sensor Examples Having Thin-Film Functionalization/Inhibition Layers.

FIG. 9A-9B is a two-view schematic illustration (planar top view and side cross-section) illustrating an exemplary embodiment of a sensor device 300 having aspects of the invention, and including a thin coating layer 318 covering at least a portion of the surface of device 300. The device 300 may have an architecture generally similar to that shown in FIG. 1, including one or more contacts electrically communicating with nanostructure channel or layer 306 (a space-apart source-drain pair 310, 312 are shown). Nanostructure channel or layer 306 may in certain examples comprise a random network of carbon nanotubes. Alternatively, Nanostructure channel or layer 306 may comprise alternative discrete nanosturctures or nanoparticle films, as described above with respect to the embodiment shown in FIGS. 1-3.

In this example, a substrate 304 serves as a gate electrode and is isolated from both network 306 and contacts 310, 312 by insulating substrate surface 316 (e.g., Si4N3, SiO2, and the like). Measurement circuitry is illustrated having power sources 313, 324 providing a controllable source-drain voltage and a gate voltage respectively, wherein meter 322 is representative of any of a number of suitable measurement systems, as described further above with respect to the examples of FIGS. 1-3. In certain embodiments, coating layer 318 may be configured to inhibit interaction of either or both of contacts 310, 312 and substrate surface 316 with a sample medium (shown as analyte medium 301).

In certain embodiments, it is advantageous to isolate the network 306 from direct charge-interaction with medium 301, and to exploit surface electrochemical reactions and redox states of the layer 318, so as to influence the properties of network 306 (e.g., its conductivity), without direct charge transfer. Additional recognition materials may be employed, e.g., applied as an additional layer (see material 120 in FIG. 1). Electrically isolating the CNT network 306 (e.g., with a dielectric layer formed by atomic layer deposition (ALD) comprising Al2O3, ZrO2 or the like) can inhibit direct chemical interaction of medium with network 306, and permit increase selectivity and stability. ALD methods are particularly suitable for depositing uniform, continuous thin layers of materials, and also may prevent damage to delicate materials, such as nanotubes, that might be damaged by other methods of deposition. However, alternative methods are possible without departing from the spirit of the invention. For example, thermal and e-beam evaporation may be employed, and additional process steps may be included to improve coating properties, such as rotating and/or tilting a substrate during evaporation.

See, for example, U.S. Ser. No. 11/588,845 filed Oct. 26, 2006 (published 2008-0021339), entitled "Anesthesia Monitor, Capacitance Nanosensors and Dynamic Sensor Sampling Method"; and U.S. Pat. No. 6,894,359 entitled "Sensitivity Control For Nanotube Sensors"; each of which is incorporated by reference.

Further description of methods for applying layer 318 may be found in, for example, U.S. applications No. 60/922,642 filed Apr. 10, 2007; Ser. No. 11/636,630 (published 2007-0079498) entitled "Ammonia Nanosensors, and Environmental Control System"; and Ser. No. 11/588,845 filed Oct. 26, 2006 (published 2008-0021339), entitled "Anesthesia Monitor, Capacitance Nanosensors and Dynamic Sensor Sampling Method"; each of which is incorporated by reference.

Charge-permeable inhibition layer. While it has been shown that thin dielectrics (e.g., as applied by ALD) can create gas-diffusion barriers, embodiments having aspects of the invention employ unexpected effects of functionalization/inhibition layers having particular configurations. Conventionally, thin-film dielectrics are employed for electrical isolation or diffusion barrier elements in device architectures. However, in embodiments having aspects of the invention, it has been found that an inhibiting coating layer may be configured to permit interaction of the nanostructure channel or layer 306 (e.g., random network of carbon nanotubes) with the sample medium 301 sufficient to permit detection and/or measurement of a target analyte in medium 301, while at the same time effectively inhibiting interaction of either or both of contacts and substrate surface 316 with a sample medium 301.

As an example, atomic layer deposition allows formation of conformal coating with precise thickness control.

In certain embodiments, a very thin layer (e.g., ZrO2 Al2O3, or the like) may be deposited so as to achieve a differential coating between nanotubes of a network (or other nanoparticles forming channel 306) and the substrate upon which the network is supported. In particular, when water is used as an ALD precursor, the hydrophobicity of carbon nanotube surface inhibits film deposition. As result, the substrate surface can be coated while leaving the carbon nanotube surface exposed for interactions with analytes.

In an exemplary embodiment, layer 318 comprises a thin layer of a dielectric material (e.g., Al2O3, ZrO2 or the like) applied so as to generally extend over substrate surface, contacts and nanotube network. Layer 318 permits suppression of interference, noise or inconsistencies due to interactions of sample (e.g., humidity) with substrate surface 316, while permitting effective interaction of the sample with nanotubes 306. It has been shown that layer 318 may be configured so as to permit charge-transfer between an analyte in medium 301 with network 306 in a detectable analyte-specific interaction, while inhibiting chemical and electrical interaction of a sample medium with substrate surface 316 (and/or exposed surfaces of contacts 310-312), so as to prevent or reduce effects which may otherwise (1) interfere with a sensor detection signal (e.g., reduced selectivity, lower signal-to-noise), and/or (2) induce changes with time that reduce stability, recovery or useful life.

In one embodiment ALD methodology was employed to apply a very thin and generally uniform layer comprising ZrO2 on the order of magnitude of a few nanometers in mean thickness (e.g., between about 5 and about 100 nm, and preferably between about 10 and about 50 nm). In an alternative embodiment, layer 318 may be deposited so as to achieve a differential coating between nanotubes of a network and the substrate upon which the network is supported. It should be understood that layer 318 may be configured to cover all portions of a substrate device exposed to a sample medium, or may be configured to cover only selected portions, such as adjacent the nanotube network. Additional encapsulation or passivation materials may be employed to protect regions of device, e.g., surfaces not closely adjacent network 306.

Further description of methods for applying layer 318 may be found in, for example, U.S. applications No. 60/922,642 filed Apr. 10, 2007; Ser. No. 11/636,630 (published 2007-

0079498) entitled "Ammonia Nanosensors, and Environmental Control System"; and Ser. No. 11/588,845 filed Oct. 26, 2006 (published 2008-0021339), entitled "Anesthesia Monitor, Capacitance Nanosensors and Dynamic Sensor Sampling Method"; each of which is incorporated by reference.

See also the ALD methods found in P. Chen, et al, "*Atomic Layer Deposition to Fine-Tune the Surface Properties and Diameters of Fabricated Nanopores*", Nano Lett (June 2004) Vol. 4, No. 7, pp 1333-37; D. Farmer et al, "*Atomic Layer Deposition on Suspended Single-Walled Carbon Nanotubes via Gas-Phase Noncovalent Functionalization*", Nano Lett (March 2006) Vol. 6, No. 4, pp 699-703; and M. Groner et al, "*Gas diffusion barriers on polymers using Al2O3 atomic layer deposition*", Appl. Phys. Lett. (2006) Vol. 88, pp 051907-1; which publications are incorporated by reference. Alternative methods may be used, such as thermal and e-beam evaporation. Additional process elements may be included to improve coating properties, such as rotating and/or tilting a substrate during evaporation.

Figure 10:
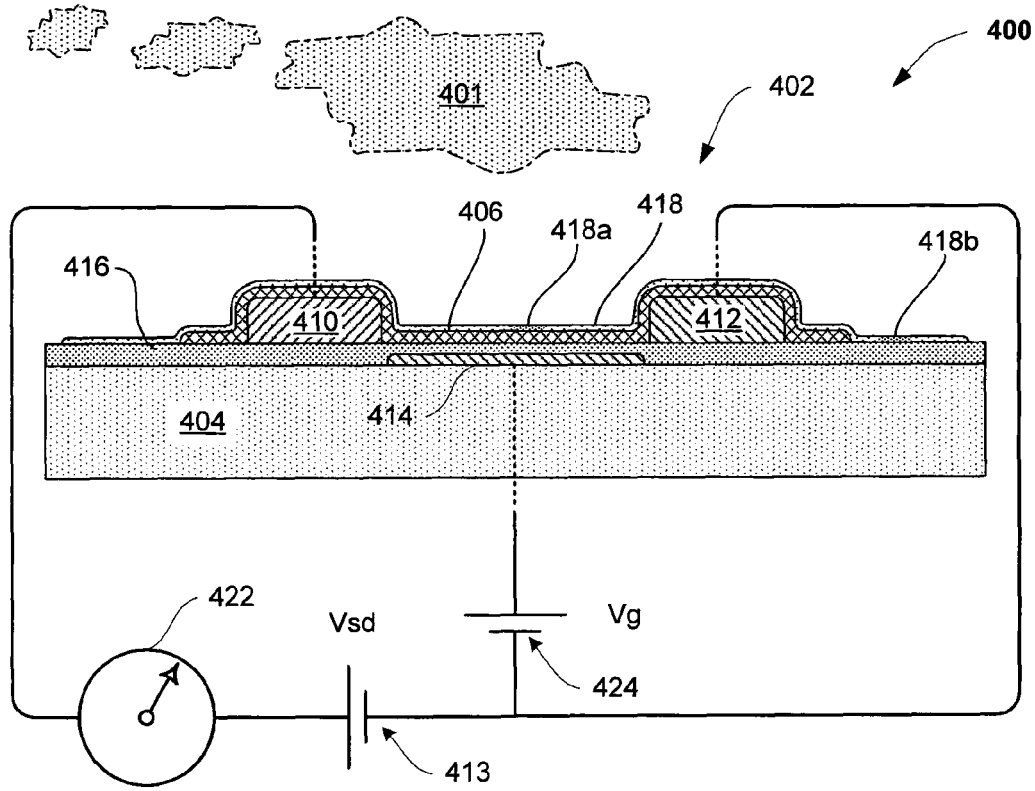
FIG. 10 is a side cross-section view illustrating an alternative embodiment of a sensor device having aspects of the invention having a nanotube network deposited on a substrate above a pattern of contacts, and including a thin-film inhibition layer.

FIG. 10 is a side cross-section view illustrating an alternative embodiment of a sensor device 400 having aspects of the invention having a nanotube network deposited on a substrate above a pattern of contacts, and including a thin-film functionalization layer 418. The device 400 has an alternative arrangement to the architecture shown in FIG. 9A-B. Device 400 comprises a substrate 404 having an insulating or dielectric surface 416 (either intrinsic to substrate 404 or a distinct layer). One or more contacts are disposed adjacent surface 416 (a space-apart source-drain pair 410, 412 are shown as an example). A nanoparticle network 406 (e.g., a random network of carbon nanotubes) is disposed adjacent surface 416 over and electrically communicating with the contacts 410-412.

Although the substrate may comprise materials conventional to semiconductor practice (e.g., silicon wafer, quartz wafer, and the like), the arrangement of device 400 is very suitable to the use of organic sheet materials, such as a flexible polymer sheet (e.g., PET). Contacts 410-412 may comprise metals, such as vapor deposited metal, or advantageously may comprise printed traces of conductive ink composition, such as silver ink, graphite compositions, and the like. In such "printed electronic" embodiments, network 406 may comprise nanotubes such as SWNTs deposited from a solution or suspension applied to the surface device 400, for example by spray deposition. Conventional masking techniques may be used to control deposition region of network 406. Alternatively, ink jet or other printing or automated methods may be used to deposit network 406.

In embodiments where a substrate 404 is selected comprise a conductive material, substrate 404 may optionally serve as a gate electrode, permitting a gate voltage to controllably influence the properties of device 400, such as the conductivity of network or channel 406. Alternatively (as shown), if a gate electrode is desired adjacent an insulating substrate 404, the gate electrode may be deposited as a layer 414 upon substrate 404, and isolated by a gate dielectric or insulater (in this example, substrate surface layer 416).

Measurement circuitry is illustrated having power sources 413, 424 providing a controllable source-drain voltage applied to contacts 410-412 and a gate voltage respectively applied to gate 414 (circuit connection to contact electrodes may be conventional, such as by wire bonding to side trace portions, and the like. Meter 422 is representative of any of a number of suitable measurement systems, as described further above with respect to the examples of FIGS. 1-3.

In certain embodiments, coating layer 418 may be configured to inhibit interaction of either or both of contacts 410, 412 and substrate surface 416 with a sample medium (shown as analyte medium 401), and optionally configured to permit sample interaction with network 406, in the manner described above with respect to FIGS. 9A-B and layer 318. For example, layer 418 may be configured to permit charge transfer from an analyte or mediator species (401) to network 406.

8. Conversion Device Example

At room temperature and pressure in an oxygen-rich environment (air), Nitric oxide (NO) gas eventually becomes nitrogen dioxide (NO2). This reaction can take hours or days. It may be sped up at elevated temperatures, but can still take minutes or hours, and thus an acceleration process is desired.

It is also desired to optimize a conversion process for application to medical breath analysis. There are a number of contrasting industrial applications where NO is converted and/or destroyed. Generally in those applications, the ultimate goal is the removal of all NOx compounds, as toxins or pollutants. In such industrial applications, NO may be converted to NO2, the NO2 may be in turn converted to N2 and O2, and typically it is irrelevant if some of the NO or NO2 is lost or destroyed, as that is the ultimate goal.

For our purposes of medical breath analysis, it is desired to avoid loss or destruction of either NO or NO2, in order to obtain measurements with the greatest physiological significance and diagnostic value. For this purpose, typical commercially available systems produce unacceptable results.

An example of a Pt catalyst used in industry to convert NO to NO2 or N2 and O2 is a typical automotive catalytic converter, and similar converters for other pollution control uses. These are generally made of a ceramic matrix with a wash coat of catalyst. A typical 3-way catalytic converter may include Pt, Rh, and Pd. The ceramic matrix in these converters adsorbs NO, thus having a net scrubbing effect on NO concentration. In addition, current technology is geared toward high volume/flow/concentration applications.

Another method of converting NO to NO2 is to react it with ozone (O3). This method has good conversion efficiency, but requires not only the generation of ozone, but also may require the scrubbing of the residual ozone after the conversion is complete since excess Ozone is needed in the reaction. This makes the conversion process more complicated and potentially dangerous because of the ozone.

Figure 11:
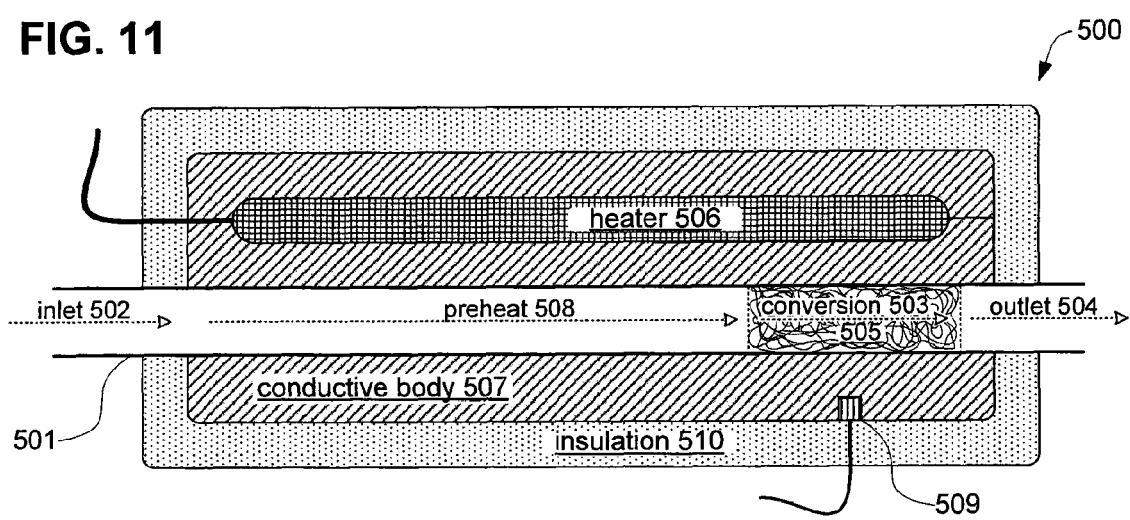
FIG. 11 illustrates an embodiment of a catalytic converter having aspects of the invention, and configured (in this example) for low-loss, low-flow catalytic conversion of nitric oxide to nitrogen dioxide (NO-NO2).

FIG. 11 illustrates an embodiment of a catalytic converter 500 having aspects of the invention, and configured (in this example) for low-loss, low-flow catalytic conversion of nitric oxide to nitrogen dioxide (NO-NO2). Converter 500 comprises an conduit 501 including in communicating sequence: (i) an inlet portion 502 configured to receive the breath sample under an input pressure sufficient to induce flow in the conduit, a conversion portion 503, and an outlet portion 504 configured to dispense the breath sample following conversion; and a conversion material 505 disposed within the conversion portion. The conversion material 505 may an active substance promoting conversion of NO to NO2 (e.g., a catalyst) and a carrier material configured to support the active substance in contact with the breath sample.

In this example, a catalyst such as Pt metal may be used as a catalyst to lower the energy barrier, and therefore increase the reaction rate under certain conditions. Alternative or additional catalyst materials, such as Rh, and Pd may be included. The embodiment provides that the oxidation state and physical form of the platinum metal may be optimized for conversion efficiency and stability.

Preferably, a suitable substrate for the catalyst material is provided (e.g., Alumina, silica or glass, such as in the form of beads). However, for detection applications, the choice of catalyst support material is very important. In order to achieve a high surface area of Pt, a preferred embodiment includes catalyst material (e.g., Pt particles) deposited on a carrier material, such as a wool-like fiberous substrate (e.g., quartz wool having fiber diameters ranging from about 8 to about 15 microns). It has been found that high purity, high quality quartz wool allows NO to pass without absorption at concentrations down to the ppb level. This is critical for applications that require low level detection.

In one embodiment of a converter configured for breath analysis, a small amount of Pt is deposited on quartz wool, and is loosely packed into one or more suitable enclosures (e.g., an inert tube such as borosilicate glass, PTFE, or the like). In one example, about 0.2-0.4 g total weight of wool plus Pt was disposed in a tube of about 10" length and ⅛-¼" inner diameter. The wool was arranged to take up about 1-2" of length in the tube, and positioned about ¼ of the way from one end. Alternatively, a different matrix, e.g. mesh, made of quartz or $SiO_2$ can be used as substrate. Various approaches, including wet chemistry, electroplating, and atomic layer deposition can be applied for depositing a coating layer or particles of Pt (or other catalytic material).

Optionally, the conversion device may include a temperature regulation mechanism, so that operating temperature may be maintained to best results. The conversion device embodiment 500 comprises a heating mechanism arranged adjacent the conduit and configured to maintain a selected elevated temperature of the conversion region. In one example, the heating mechanism includes a heating element 506, and a thermally conductive body 507 in effective thermal communication with the heating element and at least the conversion region 503 of the conduit 501. The conduit of the embodiment may further comprise a pre-heating region 508 disposed in sequence upstream of the conversion region and in communication with the heating mechanism, so as to provide a selected elevation in temperature of the sample during flow through the pre-heating region. The heating mechanism of the embodiment may further comprise a feed-back temperature sensor 509 and control circuitry (not shown) configured maintain a selected temperature in the conversion region. Optionally, the converter may be enclosed in an insulation material or jacket 510.

In this example, a tube is placed inside a heater with an active heated length of 6-8 inches, such that the wool is positioned at one end of the active heat area. Sample gas is introduced into the tube at the opposite end from the catalyst so it passes through the heated area first before reaching the Pt coated wool. Sample flow may be at a selected rate, e.g., between 200-500 scc/m.

In operation, conversion of NO to $NO_2$ within a temperature profile (e.g., the mean temperature) selected to be high enough so that conversion is sufficiently rapid, and to be low enough so that the thermodynamic properties of the gasses maximizes conversion (e.g., so that equilibrium rate of NO to $NO_2$ back-conversion is minimized). In one embodiment, conversion takes place at a temperature within the range between room temperature (about 22 C) and about 350 C, and preferably within a range of about 100 C to about 250 C. In general higher temperatures promote fast conversion, but may be undesirable because of power, safety, and cost issues.

In the example of FIG. 11, the sample tube is enclosed in a thermally conductive body (e.g., aluminum) which contains a controllable electrical heater cartridge. Optionally, a temperature sensor (e.g., a thermistor or the like) may be disposed adjacent the tube to permit temperature of the body to be measured and used for feedback control of the cartridge. The heated tube before the catalyst section acts as a heat exchanger that warms the incoming sample gas (shown flowing left to right in the figure) to the selected conversion temperature. The catalyst (e.g., Pt on Quartz wool) provides a high surface area region where the NO gas in the sample can readily interact with the catalyst. This embodiment provides a low pressure drop as sample flows so that it does not take much energy to move the gas through the converter. The diameter of the tubing and flow rate may be selected to determine a sample exposure time within the converter (in this example, about bout 0.5-1 seconds). The inert materials ensure that no NO is lost and that conversion is efficient.

Alternative embodiments may include additional or other catalysts (e.g., Rh, Pd and the like, and alloys and mixture thereof or with Pt). Like wise, the embodiments described may be employed to convert other gases by catalytic reaction (e.g., CO-$CO_2$ and the like).

9. NO Breath Analysis.

As noted above, NO measurement in breath is an important indicator of inflammatory conditions, immune response, and a number of other conditions. In particular, exhaled nitric oxide (NO) has the potential to be an important diagnostic and management indicator for airway diseases and in particular bronchial asthma. Typically, asthmatic patients have high exhaled NO levels as compared non-asthmatic persons, and the administration of effective anti-inflammatory therapy has been correlated with a significant decrease in these NO levels.

Although existing tests of exhaled NO employing expensive, bulking and complex equipment may aid in the diagnosis and assessment of current asthma status in an clinical outpatient setting, what is needed is an inexpensive, truly portable, and patient operable NO monitoring unit to provide typical asthma patients (or their parents or caretakers) with a real-time index of the need for self-administered medication, or response to such therapy. Prompt compliance with a treatment program tailored to the patient's day-to-day (or shorter time scale) status of bronchial inflammation can prevent an asthmatic episode from becoming an emergency matter. In addition, accurate proactive control of chronic inflammatory airway conditions without over-medication can reduce cumulative tissue damage and improve long term patient outcomes.

See, for example, (a) S. A. Kharitonov et al, "*Increased nitric oxide in exhaled air of asthmatic patients*", The Lancet (1994) vol. 343, pp. 133-135; (b) B. Kimberly et al, "*Nasal Contribution to Exhaled Nitric Oxide at Rest and during Breathholding in Humans*", Am. J. Resp. Critical Care Med. (1996) 153 pp. 829-836; (c) A. F. Massaro et al, "*Expired nitric oxide levels during treatment of acute asthma*", Am. J. Resp. Critical Care Med. (1995) vol. 152, No. 2, pp. 800-803; and (d) P. E. Silkoff et al, "*Airway nitric oxide diffusion in asthma: Role in pulmonary function and bronchial responsiveness*", Am. J. Resp. Critical Care Med. (2000) 161 pp. 1218-1228; each of which publication is incorporated by reference. See also the methodology described in U.S. Pat. Nos. 5,447,165; 5,922,610; and 6,038,913; each of which is incorporated by reference.

Unlike $CO_2$, which is a major component of exhaled breath (typically 1-5%), NO is generally present in only trace amounts, typically in an order of magnitude of a few parts-per-billion (ppb). For example, a non-asthmatic patient may be test for eNO in the range of 5-25 ppb, while an asthmatic patient may test in the 30-100+ ppb range. Of course measurement at these levels requires much greater detector sensitivity than for $CO_2$. But importantly, NO is produced by metabolic processes in many different tissues and cellular responses, which are not negligible, given that trace amounts are medically relevant. In respiration, NO is produced not only in the bronchial airway, and by alveolar gas exchange from the blood, but is also produce in nasal, mouth, tracheal and throat tissue. In addition, NOx of atmospheric and localized air pollution can contribute to measurements. Therefore, substantial work has been done in the attempt to assure that the NO in sampled breath is representative of bronchial airway sources, while minimizing alternative contributions. For example, intake filters may be employed to remove ambient NO from inspired air. Techniques may be employed to exclude air emerging from the nasal cavity via the nasopharynx from the sample. In addition, exhaled NO concentrations depend substantially on expiratory flow rate.

Sample collection may include discarding an intitial portion of an exhalation, followed by collecting sample air during a period of exhalation against a flow resistance or back pressure. See for example, (a) P. Silkoff et al., "*Marked Flow-dependence of Exhaled Nitric Oxide Using a New Technique to Exclude Nasal Nitric Oxide*", Am. J. Respir. Crit. Care Med., (1997)155 pp. 260-67; (b) U.S. Pat. Nos. 5,795,787 and 6,010,459, each entitled "Method and apparatus for the measurement of exhaled nitric oxide in humans"; (c) U.S. Pat. No. 6,067,983 entitled "Method and apparatus for controlled flow sampling from the airway"; (d) U.S. Pat. No. 6,733,463 entitled "Method and measuring equipment for measuring nitric oxide concentration in exhaled air"; and (e) US Published Application No. 2004-0017,570 entitled "Device and system for the quantification of breath gases"; each of which publication and patent is incorporated by reference.

Figure 12:
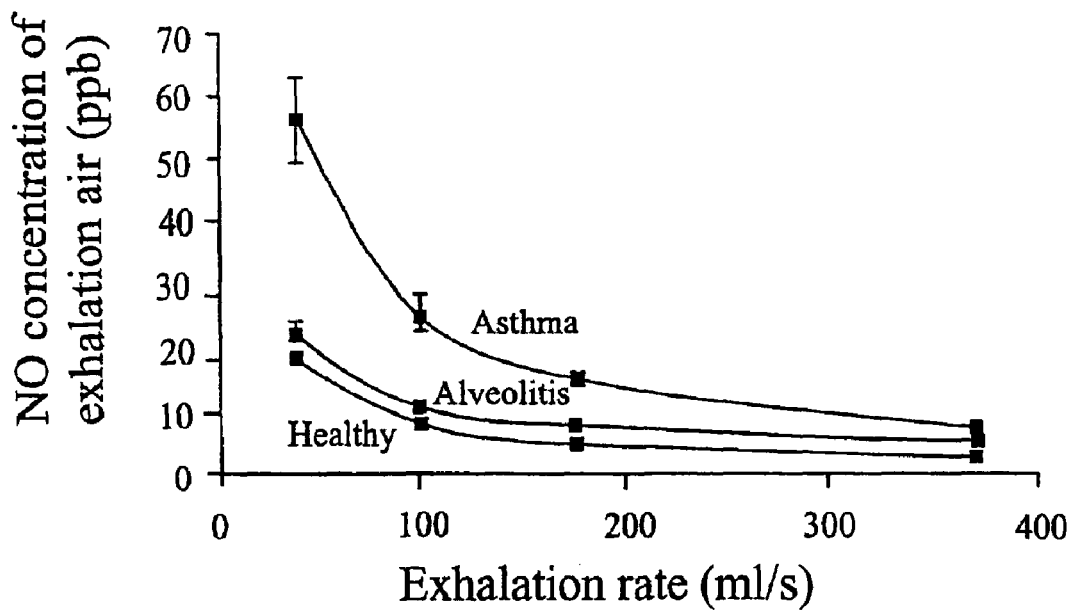
FIG. 12 shows a plot showing the dependence of NO in exhaled breath on exhalation rate, reproduced from U.S. Pat. No. 6,733,463.

FIG. 12 is a plot showing the dependence of breath NO concentration on the exhalation rate (from the above noted U.S. Pat. No. 6,733,463), comparing healthy patients with patients with airway disease conditions. For all sets of patients, there is a marked, nonlinear reduction in concentration as exhalation rate increases. Give this strong dependence, it is desirable that the exhalation rate be systematically controlled during the measurement process, to give reproducible results which are representative of airway condition, rather than representative of the degree of patient effort or compliance with instructions. It can also be seen in FIG. 12 that although the proportionate effect of exhalation rate on concentration is generally the same for each patient population, the absolute differences in patient population (in ppb) are greatest at the lowest exhalation rate.

Figure 13:
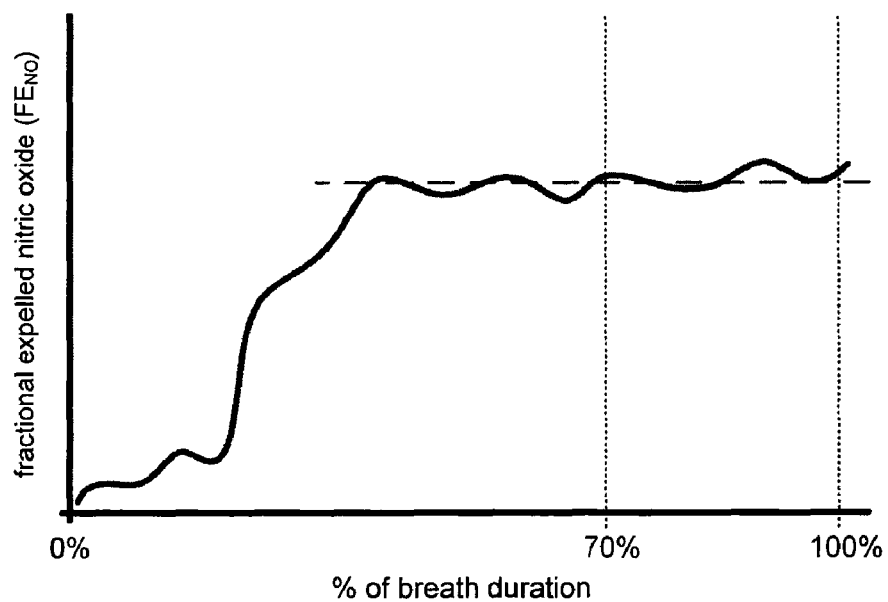
FIG. 13 shows a representative plot of the profile of fractional composition of NO in a patients exhaled breath.

FIG. 13 is a plot showing the concentration of exhaled breath NO as a function of time or breath duration. It should be recalled that unlike CO2 (which in exhaled breath is almost entirely for alveolar source), NO in exhaled breath can be supplied as a significant fraction from a number of tissues, so that the profile, such as FIG. 13, varies with sampling factors and flow rate.

10. Method of Dynamic Sensor Sampling

In one inventive aspect, a method of dynamic sensor sampling is provided, which permits measurement of analyte concentration over time, while avoiding exposure of the sensor to a sample medium on a continuous basis. For example, a valve or fluidic circulation system may be included to selectively expose a sensor having aspects of the invention to a sample medium.

In certain embodiments, a dynamic sampling method may permit more rapid sensor response to changes in analyte conditions and reduce recovery time. In certain embodiments, a dynamic sampling method may permit rapid processing of sensor signal data to produce a useful measurement, without waiting for a sensor to reach a maximum response magnitude. In yet other embodiments, a dynamic sampling method may avoid irreversible or persistent changes in sensor properties. In still other embodiments, a dynamic sampling method permits minimizing exposure of a sensor to corrosive or life-limiting environmental conditions.

In other embodiments (e.g., an electrochemical sensor), a dynamic sampling method may conserve reagent supply and extend service life. A dynamic sampling method may also be employed to reduce cross-sensitivity, where response to a cross-reactant is slower than to a target analyte.

Figure 14:
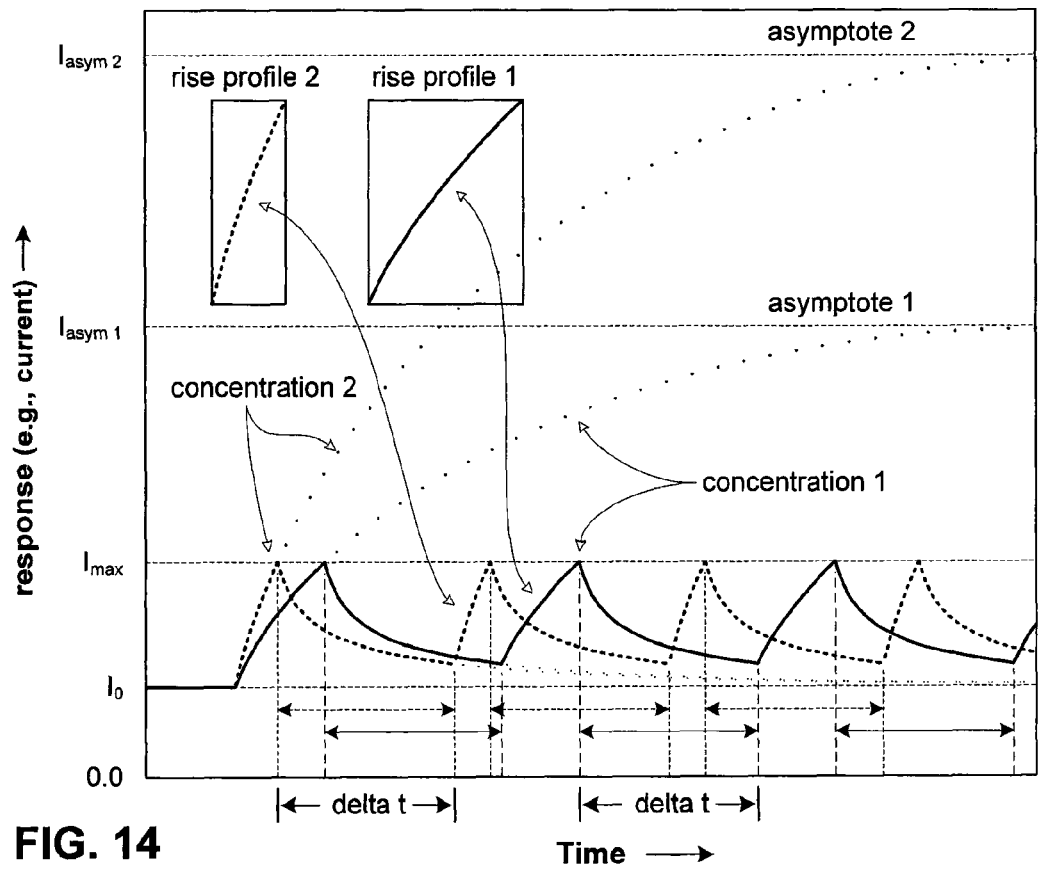
FIG. 14 is a schematic plot illustrating principles of a dynamic sensor sampling method having aspects of the invention.

FIG. 14 is a schematic plot illustrating principles of a dynamic sensor sampling method having aspects of the invention. The vertical axis represents a nominal sensor response magnitude. In the example shown, this is an electrical current I (e.g., across a channel element of a transconductance sensor) but the response may represent any one of a number different sensor properties, such as a conductance, resistance, capacitance, impedance or the like. The response may also represent a complex or derived property, such as a ratio, modulation, time constant, exponent or other relationship associated with measured properties. The response may alternatively represent a statistical property in relation to multiple sensors of a sensor array, such as a mean value or the like.

As may be seen in FIG. 14, the unexposed sensor is initially at an response level ($I_0$). Exposure of the sensor to a first analyte concentration (concentration 1) produces a sensor response that increases over time so as to asymptotically approach (dotted curve) a steady-state response magnitude ($I_{asym1}$). If the sensor is isolated from exposure to a sample (or otherwise prevented from responding to an analyte, such as by a controllable inhibitor) at a point when the response reaches a selected cut-off magnitude ($I_{max}$), a recovery trend is begun, the response value declining so as to asymptotically approach the initial value $I_0$. If the sensor is again exposed to the analyte sample after a recovery interval (delta t), the sensor response again increases ("rise profile") in a similar manner until the cut-off value $I_{max}$ is reached.

A second curve in FIG. 14 represents the response of the sensor to an analyte sample of a differing concentration (heavy dashed line—concentration 2), such that the response that increases over time so as to asymptotically approach (dotted curve) a different steady-state response magnitude ($I_{asym2}$). If the exposure is interrupted at a cut-off value ($I_{max}$), and the sensor is permitted to recover for a selected interval (delta t), the response curve of concentration 2 is similar to that of concentration 1, but having a differing rise profile (rise profile 1 vs. rise profile 2). Analytical comparison of the rise profiles may be employed to characterized the analyte concentrations, without monitoring the sensor response until a steady-state response magnitude is reached or approached.

Figure 15:
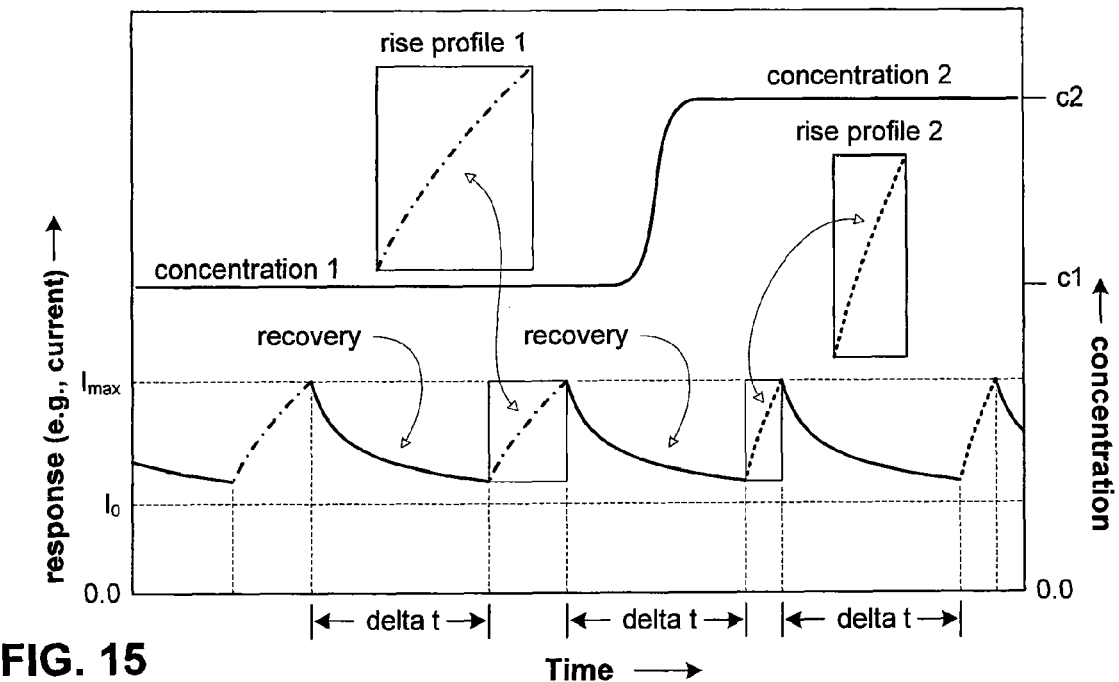
FIG. 15 is a schematic plot an example of dynamic sensor sampling for a step change in analyte concentration, having a fixed response cut-off values and recovery interval.

FIG. 15 is a schematic plot an example of dynamic sensor sampling for a step change in analyte concentration. As in FIG. 14, the sampling method in this example applies a fixed maximum response cut-off value $I_{max}$ and a fixed recovery interval delta t. The curve of sensor response shows a change in rise profile following the change in analyte concentration (rise profile 1 vs. rise profile 2). It should be understood that in the example shown, the sensor recovery is consistent, independent of analyte concentration, and approaches ($I_0$) without a persistent off-set. However, this may not be so, and methods of dynamic sampling may be applied effectively to sensors which do not exhibit these characteristics. For example, accumulated drift in sensor response may be compensated for. A number of alternative analytical algorithms may be applied to correlate rise profile with analyte concentration.

Figure 16:
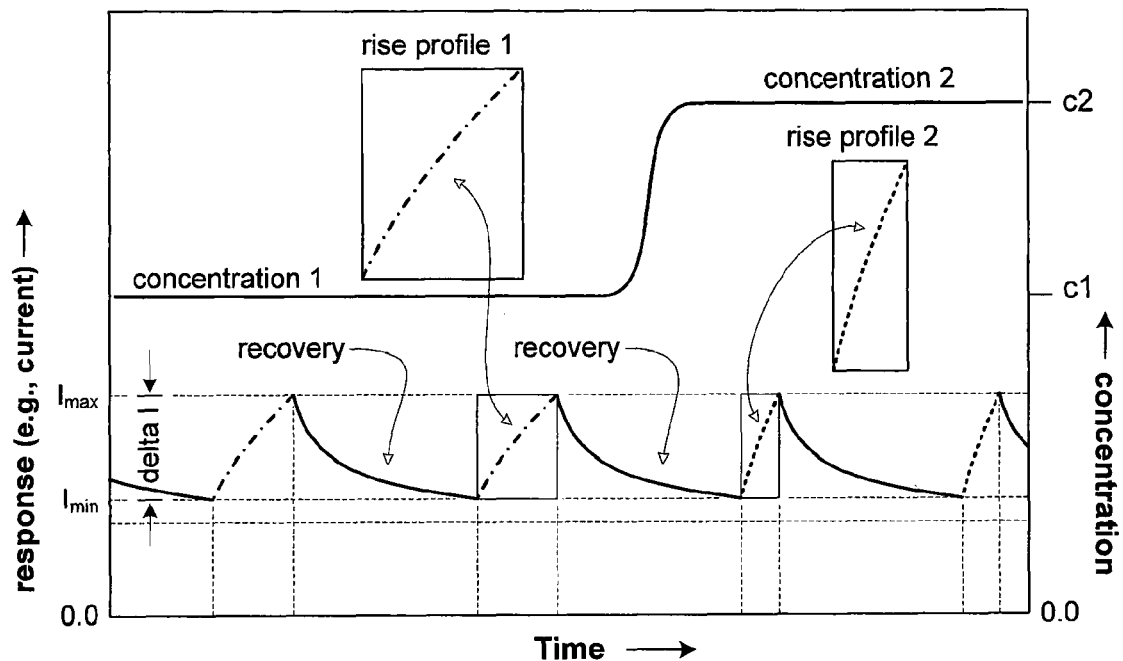
FIG. 16 is a schematic plot an example of dynamic sensor sampling for a step change in analyte concentration, having both fixed maximum and minimum values.

FIG. 16 is a schematic plot an alternative example of dynamic sensor sampling for a step change in analyte concentration, having both fixed maximum and minimum response cut-off values. As may be seen, the measurement and recovery phases (analyte exposure and isolation) are triggered by a response magnitude reached a maximum and minimum value ($I_{max}$ and $I_{min}$)

Figure 17:
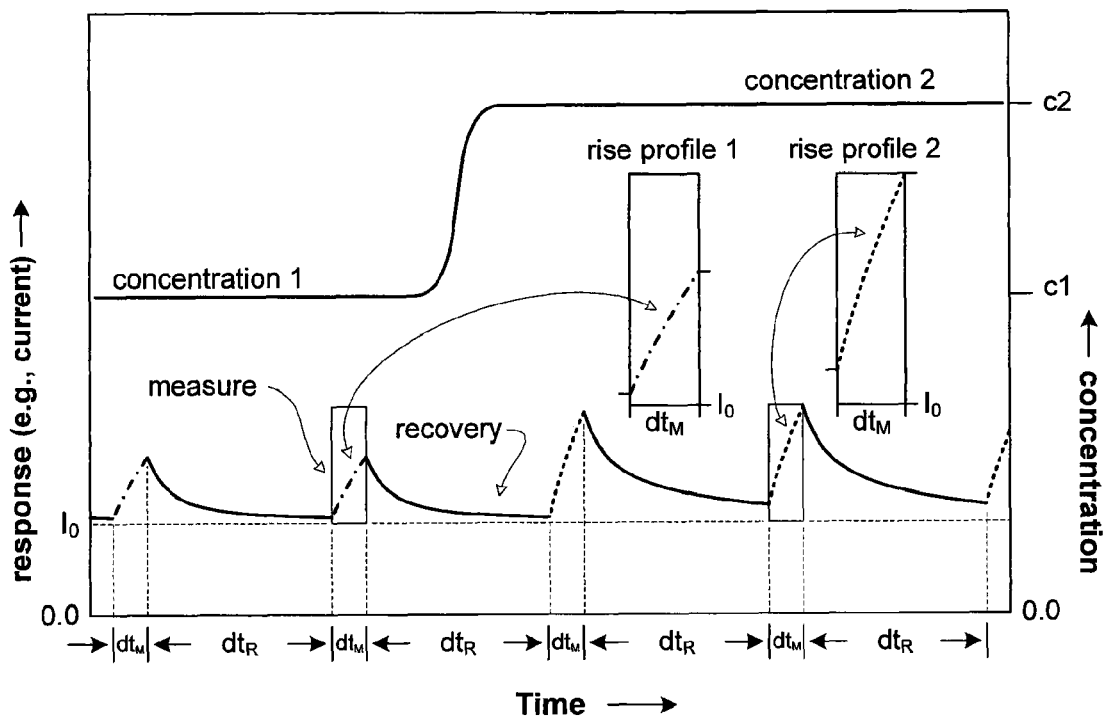
FIG. 17 is a schematic plot an example of dynamic sensor sampling for a step change in analyte concentration, having a both fixed measurement and recovery intervals.

FIG. 17 is a schematic plot an example of dynamic sensor sampling for a step change in analyte concentration, having a both fixed measurement and recovery intervals. As may be seen, the measurement and recovery phases are triggered by the passage of a determined measurement interval ($dt_M$) and recovery interval ($dt_R$).

It should be understood that a sensor system may employ the sampling modes of FIGS. 14-17 alone, in sequence or in combination. For example, a sensor system may be programmed to apply a certain sampling mode for analyte concentrations in a certain range and another sampling mode for another range of analyte concentrations, for a stand-by or active mode, or the like. Additional alternative modes of sampling may be employed without departing from the spirit of the invention.

11. Sample-Purge Transistor Measurement Method

In certain system embodiments, two (or more) sensors may be used to perform differential measurements between reference values and sample analyte concentrations, such as by employing a matched pair of very similar sensors, or calibrating a difference in responsiveness between sensors. However, as sequential sample-purge method obviates the need for multiple sensors and eliminates variation in the properties of different sensors.

FIGS. 18 and 19 illustrate examples of a measurement method employing a differential in sensor properties between a reference measurement, in which a sensor is exposed to an analyte-free gas or purge cycle (such as a medium which has been scrubbed to eliminate any analyte present), and a sample measurement, in which a sensor is exposed to an analyte sample medium. In the example shown, the sensor properties comprise transistor characteristics (see FIG. 23) are measured with a constant voltage bias is applied between the source and drain terminals 310, 312 across channel 306 of the sensor device 251. Suitable instrumentation circuitry may be employed to measure and calculate the time-variable current, resistance or conductivity of channel 306 under the influence of the field created by gate 304.

FIG. 18 shows the nominal sensor response magnitude with respect to time for two cycles of purge and sample measurement. The sensor response increases during the sample interval, and decreases (recovers) during the purge interval. In this example, the sensor purge interval (sensor recovery), and sample exposure interval are controlled to be pre-selected time periods, $dt_P$ and $dt_S$ respectively, although alternative cycle control is possible (see also FIGS. 18-21). In the examples shown the sensor response is represented by the conductivity G of channel 306, and the points at which the purge reference and sample characteristics are measured are indicated by "endpoint G/Vg,p" and "endpoint G/Vg,s" respectively.

Note that the transistor characteristics need not necessarily be measured at (or only at) the end of the sample exposure period, but may optionally be measured at earlier points or at multiple times within the exposure period. Likewise, the sample exposure period need not be of sufficient duration for sensor response to approach a plateau or maximum value, but may be much shorter. In the example shown, the sample interval $dt_s$ is selected to provide a determination of ammonia concentration while permitting the sensor to reach only a fraction of its maximum response (for example, such shortened sample intervals can increase sensor service life in corrosive environments, improve sensor recovery, or the like).

The gate voltage may be controlled to produce a pre-selected wave form by a suitable signal generator/power source, for example as a series of voltages following a linear rate of change approximating a saw-tooth waveform. Over the course of the gate voltage-waveform, the current (or resistance or conductance) through the CNT channel 306 is measured (and stored/processed as desired).

FIG. 19 is a plot shows exemplary measurements at the endpoint G/Vg,p and endpoint G/Vg,s for two different sample concentrations of ammonia (10 ppm and 80 ppm as shown in key), with the conductance G plotted against gate voltage Vg for the range of −10 to +10 volts. Note the substantial hysteresis of the curves, the comparison between sample and purge reference comparisons being made with the voltage change in a consistent direction. The methodology may be advantageously applied to other analytes, such as NO, NO2 and the like.

In examples #1 and #2, the measurement comparison between the purge reference and sample characteristics is made at a selected measurement magnitude of either Vg or conductance response G respectively, these selected magnitudes being shown as dashed lines Vg,m and G,m respectively. The differential comparison being represented graphically in FIG. 26 as dG and dVg respectively.

In an alternative example #3, a "landmark" on each of the purge reference and sample characteristic curves is determined. In this example, the landmark for each curve is based on a maximum-to-minimum modulation range in each characteristic curves over the full range of Vg variation (G,max−G,min)., shown as delta Gp and delta Gs, respectively. For each curve a landmark reference level is determined as a constant percentage k of the modulation variation for the respective curve, i.e., k(delta Gp) being the landmark reference level for the purge characteristic and k(delta Gs) being the landmark reference level for the sample characteristic. The purge-sample comparison represents the landmark movement, shown graphically in FIG. 26 as M,lm in terms of both a differential in Vg and G (dVg, dG). In the example of FIG. 26 a value of k=63% is used.

In alternative examples, more than one such comparision may be employed to calibrate and measure a sample analyte concentration, such as be combination of examples # 1, 2 and 3, or by a multiple comparison at a relatively high-conductivity region of the characteristic and a relatively low-conductivity region of the characteristic, for example by combining such multiple measurements by weighting factors.

In further alternative examples, curve-fitting methods may be employed to determine a comparison between purge reference and sample characteristic curves, either over the entire characteristic curve or over selected sub-sets of the characteristic curve data. An error function may be determined to characterize the difference between the curve data.

For example, a $3^{rd}$-order polynomial expression may be determined to fit the purge reference data, of the form:

$$Gref(Vg) = b0 + b1*Vg + b2*Vg^2 + b3*Vg^3$$

A second equation based on the previous may be determined to represent the shift from reference to sample curves:

$$Gref\text{Shifted}(Vg, Vs) = b0 + b1*(Vg-Vs) + b2*(Vg-Vs)^2 + b3*(Vg-Vs)^3$$

Giving data pairs [sampleVg(1 . . . N), Gsample(1 . . . N)], a selected shift Vs may now be to produce the minimum error between the measured sample Gref and the calculated Gref-Shift:

$$Err(Vs) = sqrt([SUM \text{ over } j(1 \ldots N):(Gref\text{Shifted}(Vg(j), Vs) - G\text{sample}(j))^2])$$

The minimum Vs can be determined by evaluating the error function over the expected range of Vs and then interpolating, or by using a dedicating minimization algorithm (i.e. Newton's Method).

A similar sample-purge differential may be employed to measure other sample analytes, such as such as NO, NO2, humidity and the like. A distinct scrubber mechanism can be employed, for example, to desiccate a sample gas stream, so as to produce a humidity-directed purge reference and sample measurements by the methods described above with respect to FIGS. 18 and 19. Such a secondary sample-purge differential may be useful in itself, or may be useful to eliminate cross-sensitivity effects of the second analyte.

CONCLUSION

Having thus described preferred embodiments of the methods and devices having aspects of the invention, it should be apparent to those skilled in the art that certain advantages of the within system have been achieved. It should also be appreciated that various modifications, adaptations, and alternative embodiments thereof may be made within the scope and spirit of the present invention. For example, the methods and devices described may be employed for the sensing of biopolymers such as nucleic acids, proteins and the like; for the detection of organisms or fragments of organisms; and/or for forensics such as genetic identification, and the like.

The invention claimed is:

1. A sensor device for detecting an analyte species in a fluid sample medium, comprising:
   (a) a substrate having a substrate surface;
   (b) one or more nanostructures disposed over the substrate surface;
   (c) one or more conducting elements in electrical communication with the nanostructure and configured to communicate with measurement circuitry; and
   (d) a layer coating at least a portion of the substrate surface, wherein the substrate and the nanostructures are differentially coated with said layer such that at least a portion of the nanostructures are exposed to permit interaction with the sample medium, wherein the layer inhibits at least one interaction between the substrate surface and the sample medium, so as to prevent or reduce at least one interference response of the device which would be detectable by the measurement circuitry via the one or more conducting elements in the absence of the layer, and wherein the coated portions of the substrate surface contact the layer.

2. The sensor device of claim 1 wherein at least a portion of one or more conducting elements are coated with said layer and said layer inhibits at least one interaction between the one or more conducting elements and the sample medium, so as to prevent or reduce at least one interference response which would be detectable by the measurement circuitry in the absence of the layer.

3. The sensor device of claim 1 wherein the layer is deposited by an atomic layer deposition method.

4. The sensor device of claim 1, wherein the layer has a thickness between about 1 nm and 10 nm.

5. The sensor device of claim 1, wherein the layer has a thickness of less than 5 nm.

6. The sensor device of claim 1, wherein the layer comprises one or both of Al2O3 or ZrO2.

7. The sensor device of claim 1, wherein the device is configured to have a sensitivity to at least one of NO and NO2.

8. The sensor device of claim 1 wherein the layer inhibits oxidation of at least one of: the substrate surface, the one or more conducting elements, and the one or more nanostructures.

9. The sensor device of claim 1 wherein the one or more nanostructures comprises a random network of carbon nanotubes.

10. The sensor device of claim 9 wherein the one or more conducting elements comprises at least one spaced-apart source-drain pair of contacts; and wherein the random network is configured so that substantially no nanotube of the network is in contact with both the source and the drain contact.

11. The sensor device of claim 1 wherein substantially all of the substrate surface in between nanostructures is coated with said layer.

12. The sensor device of claim 1 further comprising a chemical species attached to or disposed on the differential coating, wherein said species is configured to interact with the analyte species.

13. A sensor device for detecting an analyte species in a gas or liquid sample medium, comprising:
   (a) a substrate having a substrate surface;
   (b) one or more nanostructures disposed over the substrate surface;
   (c) one or more conducting elements in electrical communication with the nanostructure and configured to communicate with measurement circuitry; and
   (d) a dielectric layer coating at least a portion of the substrate surface and said nanostructures to isolate said portions of the substrate surface and the nanostructures from direct chemical interaction with species in the sample medium, wherein the coated portions of the substrate surface contact the dielectric layer, and wherein:
      i) the dielectric layer is configured to produce an electrical response at the nanostructure surface in response to interaction of analyte species in the sample medium with the dielectric layer, said electrical response detectable by the measurement circuitry; and
      ii) the dielectric layer inhibits at least one interaction between the substrate surface and the sample medium, so as to prevent or reduce at least one interference response of the device which would be detectable by the measurement circuitry in the absence of the layer.

14. The sensor device of claim 13 wherein the dielectric layer coats substantially all of the one or more nanostructures to isolate the one or more nanostructures from direct chemical interaction with species in the sample medium.

15. The sensor device of claim 13 further comprising a chemical species attached to or disposed on the dielectric layer, wherein said species is configured to interact with the analyte species.

16. The sensor device of claim 13 wherein the layer is substantially uniform and has a thickness between about 1 nm and about 100 nm.

17. The sensor device of claim 13 wherein the layer comprises one or both of Al2O3 or ZrO2.

18. The sensor device of claim 13 wherein the device is configured to have a sensitivity to at least one of NO and NO2.

19. The sensor device of claim 13 wherein the layer inhibits oxidation of at least one of the substrate surface, the one or more conducting elements, and the one or more nanostructures.

20. The sensor device of claim 13 wherein the one or more nanostructures comprises a random network of carbon nanotubes.

21. The sensor device of claim 20 wherein the one or more conducting elements comprises at least one spaced-apart source-drain pair of contacts; and wherein the random network is configured so that substantially no nanotube of the network is in contact with both the source and the drain contact.

* * * * *